US012319746B2

(12) United States Patent
Park et al.

(10) Patent No.: US 12,319,746 B2
(45) Date of Patent: Jun. 3, 2025

(54) BISPECIFIC ANTIBODY SPECIFICALLY BINDING TO GPNMB AND CD3, AND USE THEREOF

(71) Applicants: GREEN CROSS CORPORATION, Yongin-si (KR); MOGAM INSTITUTE FOR BIOMEDICAL RESEARCH, Yongin-si (KR)

(72) Inventors: Jae Chan Park, Yongin-si (KR); Eun Jung Song, Yongin-si (KR); So Jung Lim, Yongin-si (KR); Jae-Chul Lee, Yongin-si (KR); Hae Naem Kwon, Yongin-si (KR); Su A Lee, Yongin-si (KR); Ok Jae Lim, Yongin-si (KR); Mun Kyung Kim, Yongin-si (KR); Hyun Jung Cho, Yongin-si (KR); Gil-Jung Kim, Yongin-si (KR); Jee Won Lee, Yongin-si (KR); Sung Keun Kim, Yongin-si (KR); Jong Wha Won, Yongin-si (KR); Shin A Jang, Yongin-si (KR)

(73) Assignees: GREEN CROSS CORPORATION, Yongin-si (KR); MOGAM INSTITUTE FOR BIOMEDICAL RESEARCH, Yongin-si (KR)

( * ) Notice: Subject to any disclaimer, the term of this patent is extended or adjusted under 35 U.S.C. 154(b) by 910 days.

(21) Appl. No.: 17/431,218

(22) PCT Filed: Apr. 6, 2020

(86) PCT No.: PCT/KR2020/004630
§ 371 (c)(1),
(2) Date: Aug. 16, 2021

(87) PCT Pub. No.: WO2020/209559
PCT Pub. Date: Oct. 15, 2020

(65) Prior Publication Data
US 2022/0135679 A1   May 5, 2022

(30) Foreign Application Priority Data

Apr. 8, 2019   (KR) .......................... 10-2019-0040612

(51) Int. Cl.
*C07K 16/30* (2006.01)
*A61P 35/00* (2006.01)
*C07K 16/28* (2006.01)

(52) U.S. Cl.
CPC .............. *C07K 16/30* (2013.01); *A61P 35/00* (2018.01); *C07K 16/2809* (2013.01); *C07K 2317/31* (2013.01); *C07K 2317/52* (2013.01); *C07K 2317/73* (2013.01); *C07K 2317/92* (2013.01)

(58) Field of Classification Search
CPC .............. C07K 16/2809; C07K 16/30; C07K 2317/31; C07K 2317/52; C07K 2317/73; C07K 2317/92; A61P 35/00
See application file for complete search history.

(56) References Cited

U.S. PATENT DOCUMENTS

| | | | |
|---|---|---|---|
| 2013/0022597 A1 | 6/2013 | Xiao et al. | |
| 2013/0244255 A1* | 9/2013 | Zhong ................ | G01N 33/5743 436/501 |
| 2015/0166661 A1 | 6/2015 | Chen et al. | |
| 2018/0208655 A1 | 7/2018 | Zhu et al. | |
| 2019/0040135 A1 | 2/2019 | Huang et al. | |

FOREIGN PATENT DOCUMENTS

| | | |
|---|---|---|
| JP | 2008-521411 A | 6/2008 |
| JP | 2009-513147 A | 4/2009 |
| JP | 2016-538275 A | 12/2016 |
| JP | 2018-535972 A | 12/2018 |
| KR | 10-2011-0124368 A | 11/2011 |
| WO | 2006/071441 A2 | 7/2006 |
| WO | 2007/053718 A1 | 5/2007 |
| WO | 2015/063339 A1 | 5/2015 |
| WO | 2016/004108 A2 | 1/2016 |
| WO | 2016/086189 A2 | 6/2016 |
| WO | 2017/079272 A2 | 5/2017 |
| WO | WO-2018199593 A1 * | 11/2018 .............. A61K 47/68 |
| WO | WO-2019034580 A1 * | 2/2019 ......... C07K 16/2809 |

OTHER PUBLICATIONS

Lee et al. 2011. Molecular targets of phytochemicals for cancer prevention. Nature Reviews Cancer 11: 211-218. (Year: 2011).*
Brinkmann and Kontermann (mAbs (2017) 9(2): 182-212) (Year: 2017).*
Taya and Hammes (Steroids (2018) 133: 102-107) (Year: 2018).*
Crawford et al. (Molecular Cancer Therapeutics (2021) 20(8): 1350-1358) (Year: 2021).*
Menon et al. (Cancers (2023) 15(4): 1189) (Year: 2023).*
PDQ® Screening and Prevention Editorial Board. PDQ Cancer Prevention Overview. Bethesda, MD: National Cancer Institute. Updated Oct. 23, 2023. Available at: https://www.cancer.gov/about-cancer/causes-prevention/patient-prevention-overview-pdq. Accessed Mar. 22, 2024. [PMID: 26389424] (Year: 2023).*

(Continued)

*Primary Examiner* — Brad Duffy
*Assistant Examiner* — Elizabeth A Shupe
(74) *Attorney, Agent, or Firm* — Sughrue Mion, PLLC

(57) ABSTRACT

A bispecific anti-GPNMB/anti-CD3 antibody specifically binds to CD3 (cluster of differentiation 3) and GPNMB (glycoprotein non-metastatic melanoma protein B) and uses thereof are disclosed. The bispecific antibody shows high affinity and specificity to CD3 and GPNMB and thus can induce death of cancer cells expressing GPNMB and inhibit proliferation thereof. Therefore, the bispecific antibody can be used as an effective therapeutic agent for cancers expressing GPNMB.

24 Claims, 5 Drawing Sheets

Specification includes a Sequence Listing.

(56) References Cited

OTHER PUBLICATIONS

P. Bühler et al., "A bispecific diabody directed against prostate-specific membrane antigen and CD3 induces T-cell mediated lysis of prostate cancer cells", Cancer Immunol Immunother, 2008. pp. 43-52, vol. 57.
International Search Report for PCT/KR2020/004630, dated Jul. 24, 2020.

* cited by examiner

[Fig. 1]
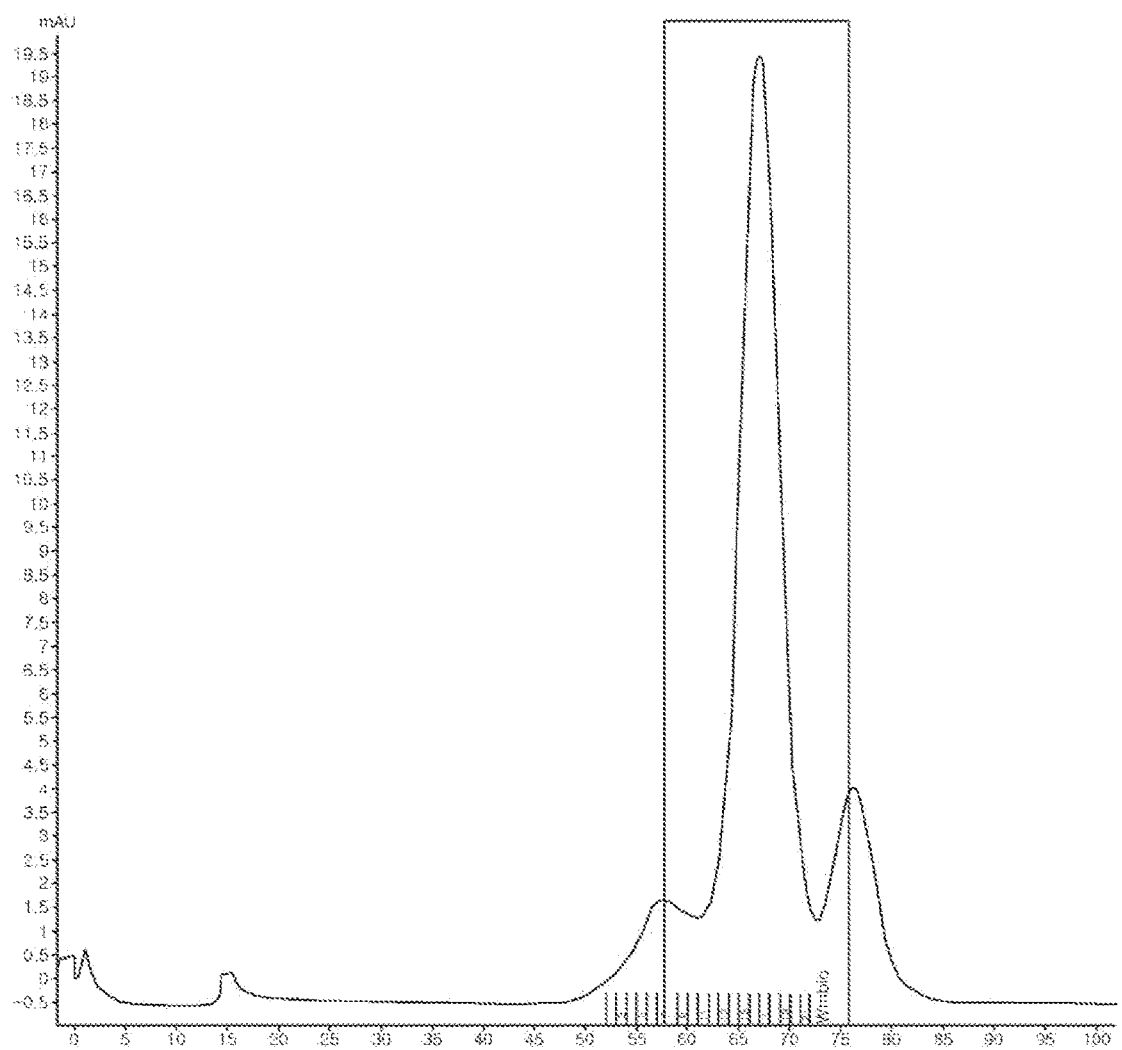

[Fig. 2]
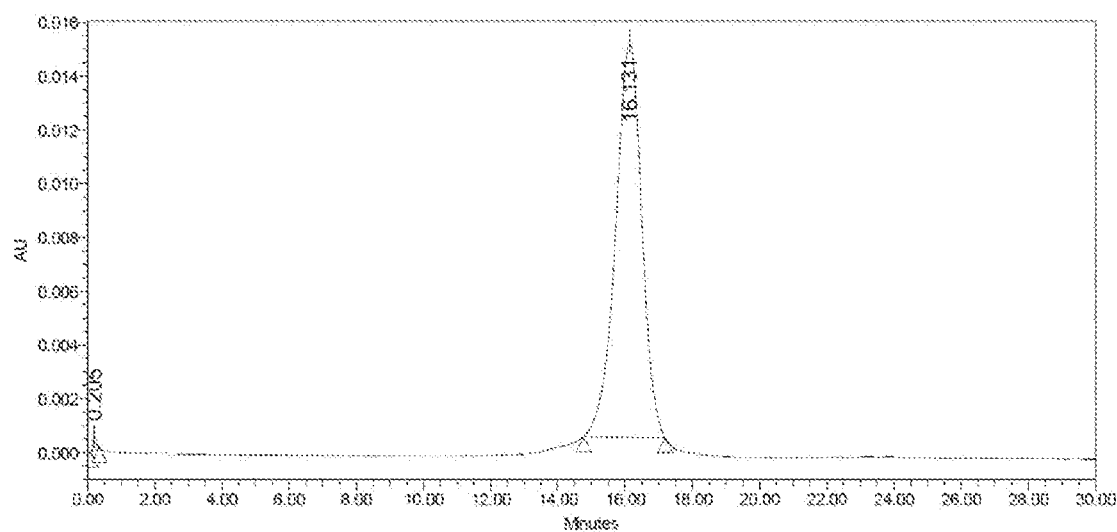

[Fig. 3]
Isotype control
GPNMB6(SEQ ID NO: 35)/A15(SEQ ID NO:36)
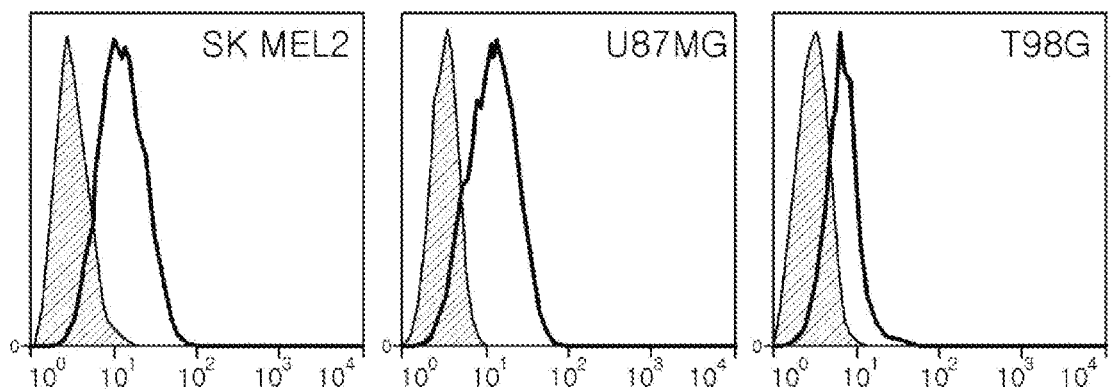
Isotype control
GPNMB6(SEQ ID NO: 35)/A15(SEQ ID NO:36)
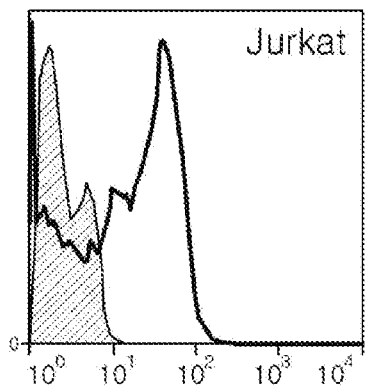

[Fig. 4]
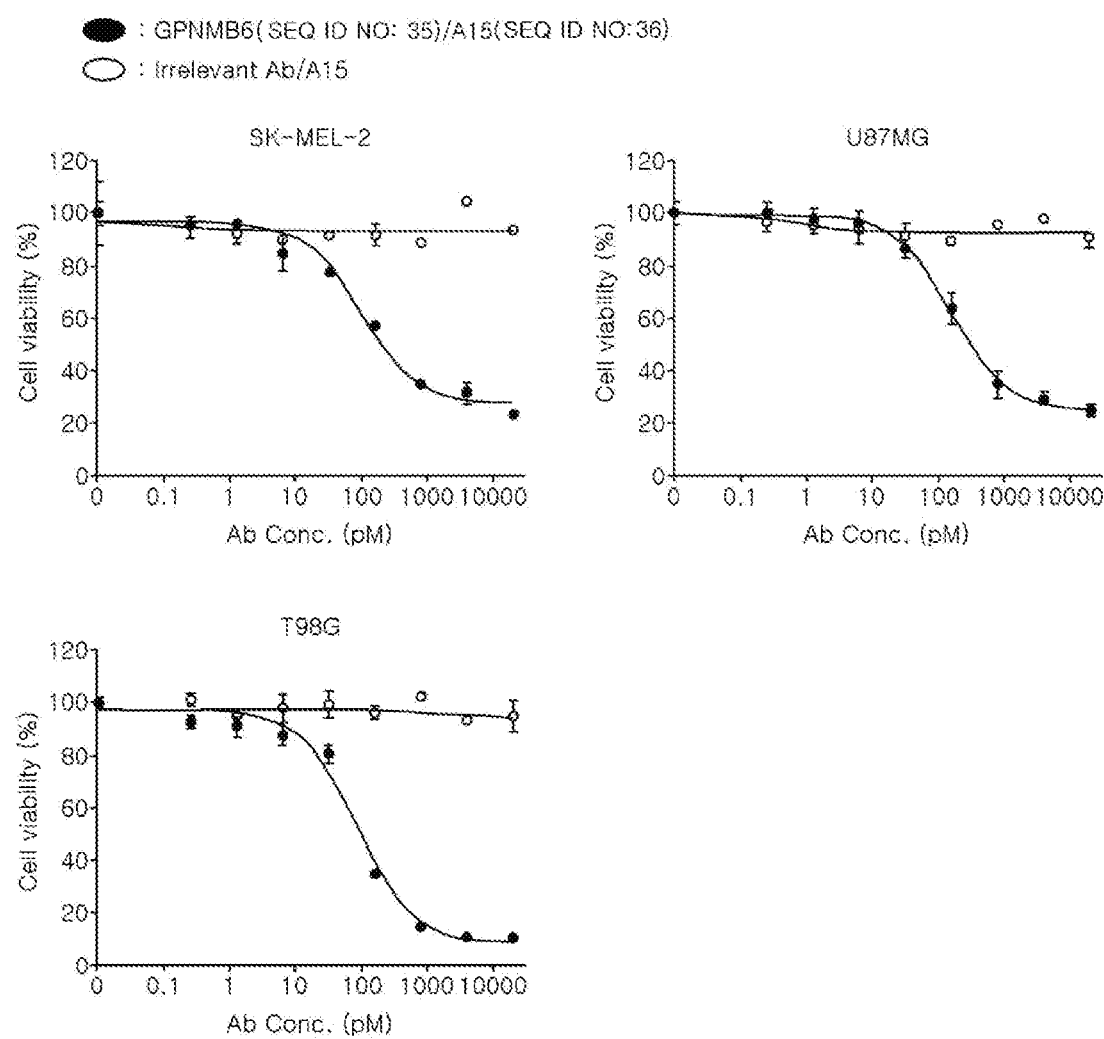

[Fig. 5]
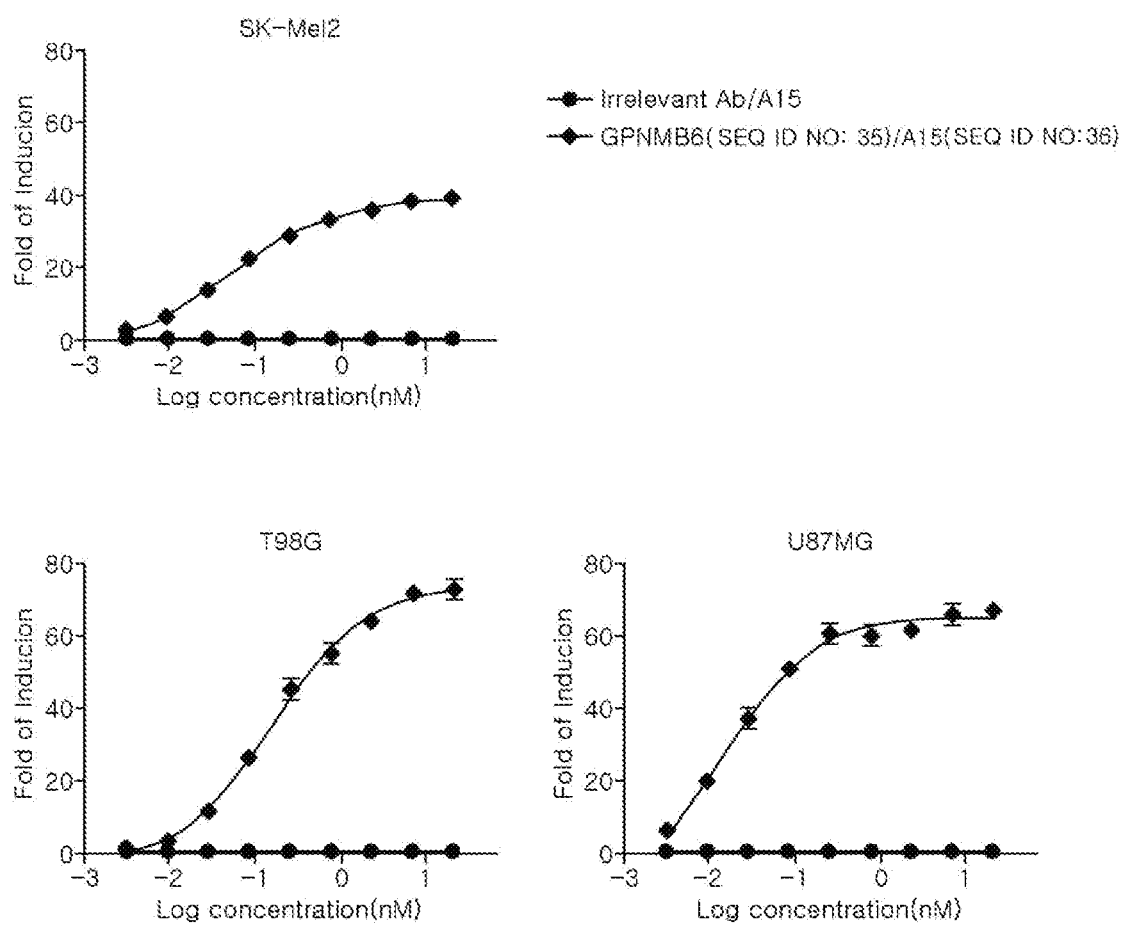

BISPECIFIC ANTIBODY SPECIFICALLY BINDING TO GPNMB AND CD3, AND USE THEREOF

CROSS REFERENCE TO RELATED APPLICATIONS

This application is a National Stage Application of PCT/KR2020/004630 filed Apr. 6, 2020, which claims priority from and benefits based on Korean Patent Application No. 10-2019-0040612 filed Apr. 8, 2019.

SEQUENCE LISTING

The content of the electronically submitted sequence listing, file name: Sequence_Listing_As_Filed.txt; size: 107,525 bytes; and date of creation: Aug. 4, 2021, filed herewith, is incorporated herein by reference in its entirety.

TECHNICAL FIELD

The present invention relates to a novel bispecific antibody that specifically binds to GPNMB and CD3, and uses thereof.

BACKGROUND ART

Among various causes of death, death from cancer occurs frequently, accounting for the second-largest proportion. Various methods for treating cancer have been continuously tried, and typical examples thereof include administration of an anticancer agent, irradiation, or surgical operation. In a case where cancer is in the early stages, treatment thereof can be made by using these methods alone or in combination; however, in a case where cancer is in the late stages or in a case where cancer has spread to other tissues through blood or has recurred, such methods have poor therapeutic effects.

Accordingly, research on immune cell-based therapeutic techniques is attracting attention. Specifically, a technique is being developed in which immune cells taken from the peripheral blood of a patient are subjected to in vitro mass proliferation, and then the resulting immune cells are re-administered to the patient so that cancer cell-specific toxic T cells present in the immune cells remove cancer cells. Moreover, with the development of recombinant technology, bispecific antibodies used in the therapeutic areas requiring T cell-mediated killing, such as for cancer, have also been developed, and effects thereof have been identified (Buhler, P., et al., Cancer Immunology, Immunotherapy 57.1, 2008: 43-52). Nevertheless, there is still a need for the development of a bispecific antibody that has better anticancer effects with minimized adverse effects.

DISCLOSURE OF INVENTION

Technical Problem

The present inventors have developed a bispecific antibody, which is capable of locating a CD3-expressing immune cell to a GPNMB-expressing cancer cell so that death of the GPNMB-expressing cancer cell is effectively induced, and have identified excellent anticancer effects thereof, thereby completing the present invention.

Accordingly, an object of the present invention is to provide a bispecific antibody that specifically binds to CD3 and GPNMB.

Another object of the present invention is to provide a pharmaceutical composition for preventing or treating cancer, comprising, as an active ingredient, the bispecific antibody or a fragment thereof.

Solution to Problem

To achieve the above-mentioned objects, the present invention provides a bispecific antibody, comprising a first domain that specifically binds to GPNMB (glycoprotein non-metastatic melanoma protein B) and a second domain that specifically binds to CD3 (cluster of differentiation 3).

In addition, the present invention provides a pharmaceutical composition for preventing or treating cancer, comprising the bispecific antibody or a fragment thereof.

Advantageous Effects of Invention

Due to having high affinity and specificity to GPNMB and CD3, the bispecific antibody according to the present invention is capable of inducing death of GPNMB-expressing cancer cells or inhibiting proliferation thereof. Accordingly, the bispecific antibody can be used as an effective therapeutic agent against GPNMB-expressing cancer.

BRIEF DESCRIPTION OF DRAWINGS

FIG. 1 illustrates a result showing that an anti-GPNMB/anti-CD3 bispecific antibody has been obtained. Here, the horizontal axis means mL (buffer flow) and the vertical axis means mAu (OD at 280 nm).

FIG. 2 illustrates a result obtained by performing HPLC analysis on the anti-GPNMB/anti-CD3 bispecific antibody.

FIG. 3 illustrates FACS results showing the binding pattern of the anti-GPNMB/anti-CD3 bispecific antibody to cancer cell lines.

FIG. 4 illustrates PBMC-mediated killing efficacy against cancer cell lines (SK-MEL-2, U87MG, and T98G) observed in the presence of the anti-GPNMB/anti-CD3 bispecific antibody.

FIG. 5 illustrates T lymphocyte activation in cancer cell lines (SK-MEL-2, U87MG, and T98G) observed in the presence of anti-GPNMB/anti-CD3 bispecific antibody.

BEST MODE FOR CARRYING OUT THE INVENTION

In an aspect of the present invention, there is provided a bispecific antibody, comprising a first domain that specifically binds to GPNMB and a second domain that specifically binds to CD3.

As used herein, the term "GPNMB" is an abbreviation for Glycoprotein Non-Metastatic Melanoma Protein B, and refers to a glycoprotein overexpressed in patients with various cancers such as breast cancer and melanoma. Although the function of GPNMB has not been clearly elucidated to date, overexpression of GPNMB occurs in cancer cells. In addition, the GPNMB refers to GPNMB present in animals, preferably humans and monkeys. That is, the term "human GPNMB" refers to human-derived GPNMB, and the term "mouse GPNMB" refers to mouse-derived GPNMB. For example, the human GPNMB may have the amino acid sequence of SEQ ID NO: 37.

As used herein, the term "cluster of differentiation 3 (CD3)" refers to a homodimeric or heterodimeric protein expressed on T cells, which is associated with the T cell receptor complex and is an essential element for T cell activation. Functional CD3 is formed by dimeric association of two or more of four different chains (ε, ζ, δ, and γ), and the CD3 dimeric configuration includes γ/ε, δ/ε, and ζ/ζ. For example, the human CD3 protein (ε/ζ) may have the amino acid sequence of SEQ ID NO: 38, and the human CD3 protein (ε) may have the amino acid sequence of SEQ ID NO: 39. Antibodies against CD3 are known to bind to CD3 present on T cells and induce T cell activation. In addition, the CD3 refers to CD3 present in animals, preferably humans and monkeys. That is, the term "human CD3" refers to human-derived CD3, and "monkey CD3" refers to monkey-derived CD3.

As used herein, the term "antibody" refers to an immunoglobulin molecule that is immunologically reactive with a particular antigen, that is, a protein molecule acting as a receptor that specifically recognizes an antigen. The antibody may be used as a concept encompassing a whole antibody and an antibody fragment.

As used herein, the term "bispecific antibody" refers to an antibody capable of simultaneously binding to two different antigens. In particular, in a case where the type of antigen to which the bispecific antibody binds is appropriately selected, immune cells such as T cells may show toxicity only to specific target cells such as cancer cells and may not show toxicity to other normal cells. Therefore, the bispecific antibody can show maximized therapeutic effects with minimized adverse effects, and thus can be effectively used for treatment requiring T cell-mediated killing. The bispecific antibody that specifically binds to CD3 and GPNMB, according to the present invention, may be designated as an "anti-GPNMB/anti-CD3 bispecific antibody".

In an embodiment of the anti-GPNMB/anti-CD3 bispecific antibody of the present invention, there is provided an antibody, comprising a first domain that specifically binds to GPNMB, which forms one of the variable regions of the antibody, and a second domain that specifically binds to CD3, which forms the other variable region. Here, the first domain that specifically binds to GPNMB may have cross-reactivity to human and monkey GPNMB. In addition, the second domain that specifically binds to CD3 may have cross-reactivity to human and monkey CD3.

In the first domain and the second domain, some amino acids may be substituted, inserted, and/or deleted as long as properties consistent with the object of the present invention, such as affinity and specificity to GPNMB and CD3, respectively, are maintained. For example, conservative substitutions of amino acids may occur therein. The conservative substitution means a substitution of an original amino acid residue with another amino acid residue having properties similar thereto.

For example, lysine, arginine, and histidine have similar properties in that they have a basic side chain, and aspartic acid and glutamic acid have similar properties in that they have an acidic side chain. In addition, glycine, asparagine, glutamine, serine, threonine, tyrosine, cysteine, and tryptophan have similar properties in that they have a non-charged polar side chain; alanine, valine, leucine, threonine, isoleucine, proline, phenylalanine, and methionine have similar properties in that they have a nonpolar side chain; and tyrosine, phenylalanine, tryptophan, and histidine have similar properties in that they have an aromatic side chain.

In an embodiment of the present invention, the first domain may include a heavy chain variable region (VH) that includes H-CDR1 represented by any one amino acid sequence selected from the group consisting of SEQ ID NOs: 1, 7, 8, 9, 10, and 11; H-CDR2 represented by the amino acid sequence of SEQ ID NO: 2; and H-CDR3 represented by the amino acid sequence of SEQ ID NO: 3; and a light chain variable region (VL) that includes L-CDR1 represented by the amino acid sequence of SEQ ID NO: 4; L-CDR2 represented by the amino acid sequence of SEQ ID NO: 5 or 12; and L-CDR3 represented by the amino acid sequence of SEQ ID NO: 6.

In an embodiment of the present invention, the first domain may include a heavy chain variable region (VH) that includes H-CDR1 represented by any one amino acid sequence selected from the group consisting of SEQ ID NOs: 1, 7, 8, 9, 10, and 11; H-CDR2 represented by the amino acid sequence of SEQ ID NO: 2; and H-CDR3 represented by the amino acid sequence of SEQ ID NO: 3; and a light chain variable region (VL) that includes L-CDR1 represented by the amino acid sequence of SEQ ID NO: 4; L-CDR2 represented by the amino acid sequence of SEQ ID NO: 5; and L-CDR3 represented by the amino acid sequence of SEQ ID NO: 6.

In another embodiment of the present invention, the first domain may include a heavy chain variable region (VH) that includes H-CDR1 represented by the amino acid sequence of SEQ ID NO: 1; H-CDR2 represented by the amino acid sequence of SEQ ID NO: 2; and H-CDR3 represented by the amino acid sequence of SEQ ID NO: 3; and a light chain variable region (VL) that includes L-CDR1 represented by the amino acid sequence of SEQ ID NO: 4; L-CDR2 represented by the amino acid sequence of SEQ ID NO: 12; and L-CDR3 represented by the amino acid sequence of SEQ ID NO: 6.

In addition, the heavy chain variable region (VH) of the first domain may be represented by the amino acid sequence of SEQ ID NO: 26, 27, 28, 29, 30, or 31. In addition, the light chain variable region (VL) of the first domain may be represented by the amino acid sequence of SEQ ID NO: 32 or 33.

In addition, the first domain may include an scFv form in which the heavy chain variable region and the light chain variable region are linked to each other through a linker. Here, any amino acid linker may be used as the linker as long as the amino acid linker can link the light chain variable region and the heavy chain variable region to each other. As an example, such an scFv may have a sequence represented by any one amino acid sequence of SEQ ID NOs: 19, 20, 21, 22, 23, 24, or 25.

In an embodiment of the present invention, the second domain may include a heavy chain variable region (VH) that includes H-CDR1 represented by the amino acid sequence of SEQ ID NO: 13; H-CDR2 represented by the amino acid sequence of SEQ ID NO: 14; and H-CDR3 represented by the amino acid sequence of SEQ ID NO: 15; and a light chain variable region (VL) that includes L-CDR1 represented by the amino acid sequence of SEQ ID NO: 16; L-CDR2 represented by the amino acid sequence of SEQ ID NO: 17; and L-CDR3 represented by the amino acid sequence of SEQ ID NO: 18.

In addition, the heavy chain variable region (VH) of the second domain may be represented by the amino acid sequence of SEQ ID NO: 44, 45, or 46. In addition, the light chain variable region (VL) of the second domain may be represented by the amino acid sequence of SEQ ID NO: 42 or 43.

In addition, the second domain may include an scFv form in which the heavy chain variable region and the light chain variable region are linked to each other through a linker. Here, any amino acid linker may be used as the linker as long as the amino acid linker can link the light chain variable region and the heavy chain variable region to each other. As an example, such an scFv may have a sequence represented by the amino acid sequence of SEQ ID NO: 49 or SEQ ID NO: 51. In addition, the nucleic acids encoding the amino acid sequences may have the nucleotide sequences of SEQ ID NO: 50 and SEQ ID NO: 52, respectively.

In an embodiment of the present invention, each of the first domain and the second domain may further include an Fc region, and the Fc region may be derived from the heavy chain constant region (CH) of IgG1, IgG2, IgG3, or IgG4.

As used herein, the term "Fc region" refers to the C-terminal region of an immunoglobulin heavy chain, containing a portion of the constant region. The Fc region may usually contain CH2 and CH3 of the heavy chain constant region of an antibody, and the Fc region may include a wild-type Fc region and a variant Fc region.

In an embodiment of the present invention, one of the Fc regions in the first domain and the second domain may have a knob structure, and the other may have a hole structure. For example, in a case where the Fc region of the first domain has a knob structure, the Fc region of the second domain has a hole structure; and in a case where the Fc region of the first domain has a hole structure, the Fc region of the second domain may have a knob structure.

As used herein, the term "knob-into-hole structure" refers to a structure obtained by inducing mutations in the respective CH3 regions of two different Ig heavy chains so that a knob structure is induced in one Ig heavy chain CH3 region and a hole structure is induced in the other Ig heavy chain CH3 region, and allowing the two regions to form a heterodimer.

Typically, in amino acid residues that form the knob structure, a hydrophobic amino acid residue having a large side chain is substituted with a hydrophobic amino acid residue having a small side chain; and in amino acid residues that form the hole structure, a hydrophobic amino acid residue having a small side chain is substituted with a hydrophobic amino acid residue having a large side chain. However, the present invention is not limited thereto.

Specifically, the substitution may include Q347R, S354C, D399V, and F405T of the CH3 region in the Fc region of the first domain; and the substitution may include Y349C, K360E, and K409W of the CH3 region in the Fc region of the second domain. Accordingly, the first domain and the second domain may be linked to each other via a disulfide bond or a knob-into-hole structure (with the knob-into-hole structure being preferred) to form a bispecific antibody. However, the present invention is not limited thereto. Here, the amino acid residues are numbered according to EU numbering.

In an embodiment, the Fc region having a hole structure may have the amino acid sequence of SEQ ID NO: 47, and the Fc region having a knob structure may have the amino acid sequence of SEQ ID NO: 48. Accordingly, the first domain may include an Fc region having the amino acid sequence of SEQ ID NO: 47 or SEQ ID NO: 48, in which case the second domain may include an Fc region having the amino acid sequence of SEQ ID NO: 48 or SEQ ID NO: 47.

In addition, LALA mutations (L243A, L245A) may be present in the respective Fc regions in the first domain and the second domain. In a case where the LALA mutations are present in the Fc region, the antibody does not exhibit antibody-dependent cell cytotoxicity efficacy (ADCC). Thus, the antibody can exhibit selective toxicity only to cancer cells in which GPNMB-expressing cells are included, while exhibiting no toxicity to other normal cells. Here, the amino acid residues are numbered according to EU numbering.

In an embodiment of the present invention, the first domain may be represented by the amino acid sequence of SEQ ID NO: 34 or 35, and the second domain may be represented by the amino acid sequence of SEQ ID NO: 36, 40, or 41.

In addition, in an aspect of the present invention, there are provided a polynucleotide encoding the amino acid sequence of the first domain, and a polynucleotide encoding the amino acid sequence of the second domain. In an embodiment, the polynucleotide encoding the amino acid sequence of the first domain may be the nucleic acid sequence of SEQ ID NO: 53 or SEQ ID NO: 54.

The polynucleotide can be easily derived by those skilled in the art from the amino acid sequence of the bispecific antibody.

In addition, in another aspect of the present invention, there are provided expression vectors, comprising polynucleotides encoding the first domain and a polynucleotide encoding the second domain, respectively.

As used herein, the term "expression vector" refers to a recombinant vector capable of expressing a target protein in a host cell, and means a gene construct that contains essential regulatory elements operably linked thereto so that an inserted gene is expressed. The respective polynucleotides encoding the amino acid sequences of the first domain and the second domain may be used in a form of being inserted into separate vectors or inserted into a single vector.

As used herein, the term "operably linked" means that a nucleic acid expression regulatory sequence and a nucleic acid sequence encoding a desired protein are functionally linked to perform a desired function. Operable linkage with a recombinant vector may be achieved using genetic recombination techniques well known in the art, and site-specific DNA cleavage and ligation may be easily achieved using enzymes and the like commonly known in the art.

Various expression host/vector combinations may be used to express the bispecific antibody. Expression vectors suitable for eukaryotic hosts include, but are not limited to, expression control sequences and the like derived from SV40, bovine papillomavirus, adenovirus, adeno-associated virus, cytomegalovirus, and retrovirus. The expression vector that may be used in bacterial hosts includes bacterial plasmids obtained from *Escherichia coli*, such as pET, pRSET, pBluescript, pGEX2T, pUC vector, colE1, pCR1, pBR322, pMB9, and derivatives thereof; plasmids having a wide host range such as RP4; and the like.

In addition, in an aspect of the present invention, there is provided a host cell transformed with the expression vector. Expression vectors, comprising polynucleotides that encode the first domain and a polynucleotide encoding the second domain, respectively, may be inserted respectively into a host cell to form a transformant. A suitable host cell for the vector may include prokaryotic cells such as *Escherichia coli, Bacillus subtilis, Streptomyces* sp., and *Pseudomonas* sp. The host cell may include eukaryotic cells including yeasts such as *Saccharomyces cerevisiae*, and higher eukaryotic cells such as insect cells.

In addition, the host cell may also be derived from plants or mammals. Preferably, the host cell that may be used includes, but is not limited to, monkey kidney cells (COST cells), NSO cells (myeloma cells of mouse origin), SP2/0 cells (myeloma cells of mouse origin), other myeloma cell lines, Chinese hamster ovary (CHO) cells, MDCK, HuT 78 cells, HEK293 cells, and the like, with CHO cells being preferred.

Meanwhile, in another aspect of the present invention, there is provided a method for producing an anti-GPNMB/ anti-CD3 bispecific antibody, comprising steps of: culturing the host cell; and purifying the anti-GPNMB/anti-CD3 antibody.

Specifically, the method for producing the bispecific antibody may comprise steps of: inserting, into a vector, a polynucleotide encoding the first domain and a polynucleotide encoding the second domain, to construct a recombinant vector; transforming the recombinant vector into a host cell and performing culture; and separating and purifying the bispecific antibody from the cultured transformant.

The bispecific antibody may be produced in a large amount by culturing the transformant, in which the recombinant vector is expressed, in a nutrient medium, and the medium and culture conditions may be appropriately selected from those known in the art depending on the type of host cell. In culture, conditions such as temperature, pH of a medium, and culture time may be appropriately adjusted to be suitable for cell growth and mass production of a protein.

In addition, in an aspect of the present invention, there is provided a pharmaceutical composition for preventing or treating cancer, comprising the bispecific antibody or a fragment thereof.

The bispecific antibody can specifically bind to CD3-expressing T cells and GPNMB-expressing cancer cells. Here, the cancer may be one or more selected from the group consisting of colorectal cancer, lung cancer, brain cancer, pancreatic cancer, ovarian cancer, breast cancer, prostate cancer, liver cancer, thyroid cancer, head and neck cancer, gastric cancer, bladder cancer, non-Hodgkin's lymphoma, skin cancer, melanoma, leukemia, neuroblastoma, and glioblastoma. However, the cancer is not limited thereto and may include any cancer in which GPNMB is expressed. Here, the bispecific antibody may induce T cells through specific binding to CD3, thereby inducing death of GPNMB-expressing cancer cells or inhibiting proliferation thereof.

The pharmaceutical composition may further comprise a pharmaceutically acceptable carrier. As the pharmaceutically acceptable carrier, a binder, a glidant, a disintegrant, an excipient, a solubilizer, a dispersant, a stabilizer, a suspending agent, a pigment, a flavor, and the like may be used for oral administration; a buffer, a preserving agent, a pain-relieving agent, a solubilizer, an isotonic agent, a stabilizer, and the like may be used in admixture for injections; and a base, an excipient, a lubricant, a preserving agent, and the like may be used for topical administration.

Preparations of the pharmaceutical composition may be prepared in various ways by being mixed with the pharmaceutically acceptable carrier as described above. For example, for oral administration, the pharmaceutical composition may be formulated in the form of tablets, troches, capsules, elixirs, suspensions, syrups, wafers, or the like. For injections, the pharmaceutical composition may be formulated in the form of unit dosage ampoules or multiple dosage forms.

The pharmaceutical composition may be administered in a pharmaceutically effective amount to treat cancer cells or metastasis thereof or to inhibit cancer growth. The effective amount may vary depending on various factors such as type of cancer, the patient's age, weight, nature and severity of symptoms, type of current therapy, number of treatments, dosage form, and route of administration, and may be easily determined by experts in the corresponding field.

The pharmaceutical composition may be administered together or sequentially with the above-mentioned pharmacological or physiological components, and may also be administered in combination with additional conventional therapeutic agents, in which case the pharmaceutical composition may be administered sequentially or simultaneously with the conventional therapeutic agents. Such administration may be single or multiple administration. Taking all of the above factors into consideration, it is important to administer an amount that is a minimum amount and allows the maximum effect to be obtained without adverse effects, and such an amount may be easily determined by those skilled in the art.

In the present invention, there is provided a method for preventing or treating cancer, comprising a step of administering the pharmaceutical composition to a subject.

As used herein, the term "subject" refers to a mammal, preferably human, suffering from or at risk of a condition or disease that can be alleviated, inhibited, or treated by administration of the pharmaceutical composition.

As used herein, the term "administration" means introducing a predetermined substance into a subject in any suitable manner, and the pharmaceutical composition may be administered via any route as long as the route allows the pharmaceutical composition to reach a target tissue. Such an administration method may include, but is not limited to, intraperitoneal administration, intravenous administration, intramuscular administration, subcutaneous administration, intradermal administration, oral administration, topical administration, intranasal administration, pulmonary administration, or rectal administration. Here, in a case of being orally administered, from the viewpoint that proteins are digested, it may be desirable to formulate a composition for oral use in such a manner that an active agent is coated or the composition is protected from digestion in the stomach. In addition, the pharmaceutical composition may be administered by any device such that an active ingredient can migrate to its target cell.

In addition, in the present invention, there is provided a use of the pharmaceutical composition for the manufacture of a medicament for preventing or treating cancer.

MODE FOR THE INVENTION

Hereinafter, the present invention will be described in more detail by way of the following examples. However, the following examples are for illustrative purposes only, and the scope of the present invention is not limited thereto.

Example 1. Production of Anti-GPNMB/Anti-CD3 Bispecific Antibody

Example 1.1. Selection of Anti-GPNMB Antibody

To select GPNMB-specific antibodies, a gene recombination technique was used to insert a DNA sequence to be expressed into the genome of bacteriophage that is parasitic in *E. coli*. Then, using a phage display technique, the inserted gene was expressed on the phage surface in the form of being fused with one of phage coat proteins.

A single colony was collected from the finally amplified population of synthetic phage display scFv library. Subsequently, the colony was cultured at 37° C. and 220 rpm in 1.5 mL of SB/carbenicillin until the OD600 value reached about 0.8 to 1.0, and then cultured for 12 hours or longer under a condition of 1 mM IPTG, 30° C., and 200 rpm. This reaction product was centrifuged at 5,500 rpm for 5 minutes, and then only each supernatant was added to an ELISA plate coated with GPNMB antigen. Subsequently, the plate was allowed to react at room temperature for 2 hours, and washed 4 times with PBST (1×PBS, 0.05% TWEEN® 20). Then, a 1:5000 dilution of HRP/Anti-hFab-HRP conjugate in 1% BSA/1× PBS was added thereto, and reaction was allowed to proceed at room temperature for 1 hour. Subsequently, the plate was washed 4 times again with PBST (1×PBS, 0.05% TWEEN® 20). Then, TMB solution was added thereto, and reaction was allowed to proceed for 5 to 10 minutes; and TMB stop solution was added thereto.

Subsequently, OD values were read at a measurement wavelength of 450 nm using TECAN Sunrise, and clones having a high OD value were obtained as individual clones. As a result, 23 clones that specifically bind to human GPNMB were selected, and the amino acid sequences thereof were identified. The selected clones were used to check their binding capacity to a GPNMB-expressing cancer cell line. As a result, it was identified that only one clone bound to the cell line. Based on this, six clones, which have enhanced protein and cell binding capacity, were additionally obtained through affinity maturation.

As a result, a total of 7 clones that bind to GPNMB protein and GPNMB-expressing cancer cell line were obtained, and the selected clones were designated as Clone GPNMB1 (SEQ ID NO: 55), Clone GPNMB2 (SEQ ID NO: 56), Clone GPNMB3 (SEQ ID NO: 57), Clone GPNMB4 (SEQ ID NO: 58), Clone GPNMB5 (SEQ ID NO: 59), Clone GPNMB6 (SEQ ID NO: 60), and Clone GPNMB7 (SEQ ID NO: 61), respectively.

The variable region sequences of the clones are shown in SEQ ID NOs: 26 to 33, respectively, and the CDR amino acid sequences in each variable region, which were identified according to Kabat numbering, are shown in Table 1 below.

In addition, Clone GPNMB6 (SEQ ID NO: 60), which shows the highest affinity among the anti-GPNMB antibodies, was formed to have a knob-into-hole structure.

Example 1.2. Selection of Anti-CD3 Antibody

To select antibodies specific for human and monkey CD3, the mouse SP34 antibody was humanized, and the antibodies, which bind to CD3 with various affinity, were selected. Among these, Clone A15 consisting of the amino acid sequence of SEQ ID NO: 36 and Clone E15 consisting of the amino acid sequence of SEQ ID NO: 41 were obtained. In addition, an antibody (Hu38E4.v1, manufactured by Genentech) having the amino acid sequence of SEQ ID NO: 40 was produced and used. In addition, for a bispecific antibody, the anti-CD3 antibody (Hu38, A15, or E15) was formed to have a knob-into-hole structure.

Example 1.3. Introduction of Vector for Antibody Expression

Twenty four hours before transfection, Expi293F cells at a density of $2.0 \times 10^6$ cells/ml were passaged with Expi293 medium at 125±10 rpm in a shaking incubator at 37° C. and 8% $CO_2$. At the time of transfection, the number of cells and cell viability were measured to identify whether cell viability of 95% or higher is exhibited. The cells were dispensed at $5 \times 10^8$ cells in a 500 mL culture flask, and then Expi293 medium was added to adjust the final volume to 170 mL (based on 200 mL). Using OPTI-MEM™ I medium, 200 μg of antibody-expressing vector was mixed therewith to a total of 1,500 μl, and culture was performed for 5 minutes at room temperature.

TABLE 1

| Clone | Variable region | CDR1 | CDR2 | CDR3 |
|---|---|---|---|---|
| GPNMB1 | Heavy chain | GFTFSNYAMS (SEQ ID NO: 1) | SISHSGGSK (SEQ ID NO: 2) | KWSTFDY (SEQ ID NO: 3) |
|  | Light chain | SSNIGNNYVS (SEQ ID NO: 4) | ADSQRP (SEQ ID NO: 5) | GAWDSSLNAYV (SEQ ID NO: 6) |
| GPNMB2 | Heavy chain | GFTFRKLNMS (SEQ ID NO: 7) | SISHSGGSK (SEQ ID NO: 2) | KWSTFDY (SEQ ID NO: 3) |
|  | Light chain | SSNIGNNYVS (SEQ ID NO: 4) | ADSQRP (SEQ ID NO: 5) | WDSSLNAYV (SEQ ID NO: 6) |
| GPNMB3 | Heavy chain | GFTFRARPMS (SEQ ID NO: 8) | SISHSGGSK (SEQ ID NO: 2) | KWSTFDY (SEQ ID NO: 3) |
|  | Light chain | SSNIGNNYVS (SEQ ID NO: 4) | ADSQRP (SEQ ID NO: 5) | GAWDSSLNAYV (SEQ ID NO: 6) |
| GPNMB4 | Heavy chain | GFTFQRYPMS (SEQ ID NO: 9) | SISHSGGSK (SEQ ID NO: 2) | KWSTFDY (SEQ ID NO: 3) |
|  | Light chain | SSNIGNNYVS (SEQ ID NO: 4) | ADSQRP (SEQ ID NO: 5) | GAWDSSLNAYV (SEQ ID NO: 6) |
| GPNMB5 | Heavy chain | GFTFIRRPMS (SEQ ID NO: 10) | SISHSGGSK (SEQ ID NO: 2) | KWSTFDY (SEQ ID NO: 3) |
|  | Light chain | SSNIGNNYVS (SEQ ID NO: 4) | ADSQRP (SEQ ID NO: 5) | GAWDSSLNAYV (SEQ ID NO: 6) |
| GPNMB6 | Heavy chain | GFTFAARPMS (SEQ ID NO: 11) | SISHSGGSK (SEQ ID NO: 2) | KWSTFDY (SEQ ID NO: 3) |
|  | Light chain | SSNIGNNYVS (SEQ ID NO: 4) | ADSQRP (SEQ ID NO: 5) | GAWDSSLNAYV (SEQ ID NO: 6) |
| GPNMB7 | Heavy chain | GFTFSNYAMS (SEQ ID NO: 1) | SISHSGGSK (SEQ ID NO: 2) | KWSTFDY (SEQ ID NO: 3) |
|  | Light chain | SSNIGNNYVS (SEQ ID NO: 4) | DTPLRP (SEQ ID NO: 12) | GAWDSSLNAYV (SEQ ID NO: 6) |

Using OPTI-MEM™ I medium, 540 µl of transfection reagent was mixed therewith to a total of 1,500 µl, and culture was performed for 5 minutes at room temperature. The OPTI-MEM™ I media, containing the vector and the transfection reagent, respectively, were mixed gently and allowed to react at room temperature for 20 minutes. Then, the resultant was placed in a flask containing EXPI293F™ cells. Culture was performed for 16 to 20 hours at 125±10 rpm in a shaking incubator at 37° C. and 8% $CO_2$. Then, 1 ml of transfection enhancer I and 10 ml of transfection enhancer II were added thereto, and culture performed for 6 days to obtain candidate antibodies.

Example 1.4. Production of Anti-GPNMB/Anti-CD3 Bispecific Antibody

The culture was centrifuged at 4,000 rpm for 30 minutes, filtered through a 0.22 µm filter, and then cell debris was removed to obtain the supernatant. 1 ml of MABSELECT XTRA™ resin was added to a column, and equilibration was achieved using Protein A binding buffer in a volume corresponding to 10 times the resin volume.

Subsequently, the supernatant was loaded onto the column using gravity. After the loading was completed, the column was washed with Protein A binding buffer in a volume corresponding to 10 times the resin volume. Subsequently, IgG elution buffer was added to the column, and elution was performed. The eluate was neutralized by adding 25 µl of 1.5 M Tris-Cl per 1 ml of the eluate, and then the concentration was measured at OD 280 nm. The eluant for which the concentration had been measured was subjected to buffer exchange with PBS via dialysis.

Next, the sample was concentrated or diluted to about 1.0 g/L to 2.0 g/L, and loaded onto a HiLoad 16/600 SUPERDEX™ 200 pg column (GE Healthcare, 28989335) on the AKTA™ Purifier 900. 20 mM sodium phosphate (pH 7.0) containing 200 mM sodium chloride was used as a mobile phase, and flowed at a flow rate of 1.0 ml/min. Then, the fractions, which were eluted about 50 to 70 minutes after the sample loading, were taken. The eluted fractions were subjected to staining with Coomassie Blue using 4% to 12% Bis-Tris PAGE (Invitrogen, 0321BOX), and then the fractions containing an antibody of 150 kDa size were taken therefrom. Subsequently, the fractions were concentrated using a 30 kDa AMICON™ centrifugal filter unit (Merck, UFC803024).

FIG. 1 illustrates a result showing that a protein sample corresponding to 150 kDa has been obtained by performing co-expression and purification on a bispecific antibody that includes an anti-GPNMB antibody fragment (SEQ ID NO: 24) and an anti-CD3 antibody fragment (SEQ ID NO: 49).

Example 1.5. Identification of Purity of Bispecific Antibody by HPLC Analysis For HPLC analysis, 50 mM sodium phosphate (pH 6.0) was used as an equilibration buffer, and a solution obtained by adding, to 50 mM sodium phosphate (pH 6.0), sodium chloride to a concentration of 500 mM and then performing filtration with a 0.45 µm bottle top filter (Nalgene, 597-4520) was used as an elution buffer. To an HPLC system (Waters, 2695/2489) was connected a cation column (Thermofisher, 054993), and then the equilibration buffer was used to achieve equilibration. The sample to be analyzed was diluted 10-fold or higher in the equilibration buffer, to prepare a loading sample. The mobile phase was analyzed in such a manner that the equilibration buffer flowed at 0.5 ml/min for 10 minutes and then the elution buffer was flowed in a linear concentration gradient method from 0% to 100% over 40 minutes. After the analysis was completed, an area in the chromatogram measured at UV 280 nm was calculated to identify the purity.

HPLC analysis was performed on the purified protein sample for which the result as illustrated in FIG. 1 is obtained. As a result, it was identified that almost no anti-GPNMB antibody fragment and anti-CD3 antibody fragment were present in the GPNMB/CD3 bispecific antibody sample (FIG. 2).

Example 2. Analysis of Affinity of Bispecific Antibody to GPNMB Protein

Quantitative binding capacity (affinity) of the purified bispecific antibody to recombinant human GPNMB was measured using BIACORE™ T-200 (GE Healthcare, USA) that is a biosensor. GPNMB purified from HEK293 cells was fixed on a CM5 chip (GE Healthcare) using an amine-carboxyl reaction until 200 Rmax was obtained. Next, the GPNMB/CD3 bispecific antibody, which was serially diluted in HBS-EP buffer (10 mM HEPES, pH 7.4, 150 mM NaCl, 3 mM EDTA, 0.005% Surfactant P20), was allowed to bind thereto in a concentration range of 0.078 nM to 5 nM for 120 seconds, and flowed at a flow rate of 30 µL/min for 1800 seconds so that dissociation was achieved. Dissociation of the antibody bound to GPNMB was induced by flowing 10 mM glycine-HCl (pH 1.5) for 30 seconds at a flow rate of 30 µL/min (Table 2). The affinity was obtained as kinetic rate constants ($K_{on}$ and $K_{off}$) and equilibrium dissociation constant ($K_D$) using BIACORE™ T-200 Evaluation Software (Table 3).

TABLE 2

| SPR | Biacore T200 |
|---|---|
| Chip | CM5 |
| Running buffer | HBS-EP, pH 7.4 |
| Flow rate | 30 µl/min |
| Association/dissociation time | 120 sec/600 sec |
| Concentration of IgG | 0.078 to 5 nM, ½ serial dilution |
| Regeneration | 10 mM glycine-HCl, pH 1.5, 30 sec |

TABLE 3

| | $K_{on}$ | $K_{off}$ | $K_D$ |
|---|---|---|---|
| GPNMB (SEQ ID NO: 35)/ A15 (SEQ ID NO: 36) | $3.41 \times 10^5$ | $3.74 \times 10^{-4}$ | $1.10 \times 10^{-9}$ |

Example 3. Analysis of Affinity of Bispecific Antibody to GPNMB- and CD3-Expressing Cells

Example 3.1. Analysis of Affinity of Bispecific Antibody to Human GPNMB-Expressing Cancer Cell Lines It was identified, using flow cytometry, whether the bispecific antibody exhibits affinity to GPNMB-expressing cells. Specifically, 5 ml tubes were prepared, each tube containing 100 µl of FACS buffer (2% FBS/PBS) to which each of three types of cancer cell line (SK MEL2, U87MG, and T98G) was added at a concentration of $3 \times 10^5$ cells, and each tube was treated with 0.5 µs of primary antibody. Then, light was blocked for 30 minutes and incubation was performed at 4° C. Subsequently, 1 ml of FACS buffer was added thereto. Centrifugation was performed at 4° C. for 3 minutes at 1,500 rpm, and then the supernatant was removed.

Next, each tube was treated with 0.2 μg of fluorochrome-labeled secondary antibody, which is capable of specifically binding to the primary antibody, in 100 μl of FACS buffer. Then, light was blocked for 30 minutes and incubation was performed at 4° C. Subsequently, 1 ml of FACS buffer was added thereto, and centrifugation was performed at 4° C. for 3 minutes at 1,500 rpm; and then the supernatant was removed to obtain a sample. Then, 200 μl of buffer, which was prepared in a ratio of FACS buffer:BD CYTOFIX™=1:4, was added to the sample so that the cells were suspended, and analysis was performed by BD FACSCALIBUR. The results are illustrated in FIG. 3.

As illustrated in FIG. 3, it was found that the GPNMB (SEQ ID NO: 35)/A15 (SEQ ID NO: 36) bispecific antibody bound to the three types of cancer cell line. The negative control antibody used as an irrelevant control did not bind to any of the three types of cancer cell line.

Example 3.2. Analysis of Affinity of Bispecific Antibody to Human CD3-Expressing Cancer Cell Lines It was identified, using flow cytometry, whether the bispecific antibody produced according to Example 1 also exhibits affinity to CD3-expressing cells. Specifically, 5 ml tubes were prepared, each tube containing 100 μl of FACS buffer (2% FBS/PBS) to which the cell line Jurkat was added at a concentration of $3 \times 10^5$ cells, and each tube was treated with 0.5 μg of primary antibody. Then, light was blocked for 30 minutes and incubation was performed at 4° C. Subsequently, 3 ml of FACS buffer was added thereto, and centrifugation was performed at 1,500 rpm for 3 minutes at 4° C.; and then the supernatant was removed.

Next, each tube was treated with 0.2 μg of fluorochrome-labeled secondary antibody, which is capable of specifically binding to the primary antibody, in 100 μl of FACS buffer. Then, light was blocked for 30 minutes and incubation was performed at 4° C. Subsequently, 1 ml of FACS buffer was added thereto, and centrifugation was performed at 1,500 rpm for 3 minutes at 4° C.; and then the supernatant was removed to obtain a sample. Then, 200 μl of buffer, which was prepared in a ratio of FACS buffer:BD CYTOFIX™=1:4, was added to the sample so that the cells were suspended, and analysis was performed by BD FACSCALIBUR. The results are illustrated in FIG. 3.

As illustrated in FIG. 3, it was found that the GPNMB (SEQ ID NO: 35)/A15 (SEQ ID NO: 36) bispecific antibody bound to the cell line Jurkat. The negative control antibody used as an irrelevant control did not bind to the cell line Jurkat.

Example 4. Evaluation of Cell Killing Efficacy of Bispecific Antibody Against Tumor Cell Lines Using human peripheral blood mononuclear cells (PBMCs) and the bispecific antibody produced according to Example 1, GPNMB-specific tumor cell killing efficacy of the bispecific antibody against three types of GPNMB+ tumor cells (SK-MEL-2, U87MG, and T98G) was identified according to the method as described below.

Example 4.1. Construction of Target Cell Lines

Three types of GPNMB+ tumor cells (SK-MEL-2, U87MG, and T98G) were harvested with 1× trypsin-EDTA solution, and centrifuged at 1,200 rpm for 5 minutes at 4° C. Subsequently, the supernatant was removed and resuspension was performed in cRPMI (RPMI, A10491-01+10% FBS+55 μM β-ME). Then, the number of cells was quantified. Each cell line suspension was prepared at a concentration of $1.0 \times 10^5$ cells/ml, added to a 6-well plate at 1 ml/well, and the plates were incubated in a $CO_2$ incubator at 37° C. for one day to prepare the cell lines. Next, transduction was performed using INCUCYTE® NucLight Red Lentivirus Reagent (EF-1 Alpha Promoter, Puromycin selection) at MOI (multiplicity of infection) of 3.

Example 4.2. Preparation of Target Cell Lines

Specifically, the cells were harvested with 1× trypsin-EDTA solution, and centrifuged at 1,200 rpm for 5 minutes at 4° C. Subsequently, the supernatant was removed and resuspension was performed in cRPMI (RPMI, A10491-01+10% FBS+55 μM (3-ME). Then, the number of cells was quantified. Each cell line suspension was prepared at a concentration of $1 \times 10^5$ cells/ml, added to a 96-well plate at 100 μl/well, and the plates were incubated in a $CO_2$ incubator at 37° C. for one day to prepare the target cell lines.

Example 4.3. Preparation of Peripheral Blood Mononuclear Cells

Cryopreserved peripheral blood mononuclear cells (PBMCs) were rapidly thawed in a water bath at 37° C., and then transferred to a 50 ml conical tube. Thawing medium (RPMI, 11875-093+10% FBS+55 μM (3-ME) was added thereto dropwise, and mixing was performed with shaking. Then, the supernatant was removed by performing centrifugation at 1,200 rpm for 10 minutes at 4° C., and resuspension was performed in 30 ml of thawing medium. Then, the number of cells was quantified, and the cells were suspended in cRPMI for respective donors so that the concentration was adjusted to $1.0 \times 10^6$ cells/ml.

Example 4.4. Plating of Peripheral Blood Mononuclear Cells and Antibody

Each antibody was diluted in cRPMI, and then diluted 1/5 starting from 20 nM. The antibodies were applied to the wells that had been plated with the target cells one day before. Then, 100 μl/well of the previously prepared PBMCs were added thereto so that a ratio of target:PBMC=1:10 (SK-MEL-2) or 1:20 (U87MG, T98G) was obtained.

Example 4.5. Real-Time Cellular Image Analysis Using IncuCyteS3

Bright field and red fluorescence were measured at intervals of 2 hours at 10× magnification using IncuCyteS3 while performing incubation in a $CO_2$ incubator at 37° C. for 2 days. From the measurement results, it was identified that the bispecific antibody exhibited cell killing efficacy against the three types of GPNMB-expressing cancer cells in a dose-dependent manner (FIG. 4). On the contrary, the bispecific antibody (Irrelevant/A15) obtained by linking Irrelevant Ab to A15 antibody did not induce cell death. On the other hand, a bispecific antibody was produced using a third-party antibody, which exhibited similar cell binding capacity to the GPNMB (SEQ ID NO: 35)/A15 (SEQ ID NO: 36), and A15 (SEQ ID NO: 36), and cell killing efficacy thereof was identified. As a result, it was identified that this bispecific antibody exhibited lower efficacy than Clone GPNMB. Based on this, it is shown that the GPNMB antibody (SEQ ID NO: 35) as a bispecific T cell-inducing antibody recognizes an effective epitope.

Example 5. Measurement of T Cell Activity Caused by Bispecific Antibody

To analyze the degree of T cell activation caused by the bispecific antibody produced according to Example 1, T cell-activating capacity of the bispecific antibody was analyzed using the cell line IL2-luc2P Jurkat (Promega) against three cancer cell lines (SK MEL2, U87MG, and T98G) that overexpress GPNMB.

Specifically, GPNMB-expressing SK MEL2, U87MG, and T98G cells were respectively seeded into a 96-well plate at $3\times10^4$ cells per well using 100 µl of culture medium, and incubated for 18 hours in a humidified incubator at 37° C. and 5% $CO_2$, to prepare the target cell lines. GLORE-SPONSE™ Frozen Thaw and Use (FTU) IL-2-luc2P Jurkat effector cells were dissolved in a water bath at 37° C. for 2 minutes. 4 mL of pre-warmed Assay Medium (RPMI medium containing 10% FBS) was added to a 15 mL conical centrifuge tube, and then 1 ml of the dissolved effector cells was added thereto. Mixing was performed slowly to prepare effector cell lines. Next, 75 µl of the medium was removed from the 96-well plate, into which the target cells had been seeded, and 25 µl of FTU IL2-Luc2P Jurkat cells were added to the plate at $1\times10^5$ cells per well.

The antibody was prepared by being diluted 1/3 starting from 10 nM so that 10 points at a 3× dose were obtained. Then, 25 µl of the prepared antibody in 10 concentrations was added to the previously prepared 96-well plate containing the FTU IL2-Luc2P Jurkat cells so that a 1× dose was achieved. Incubation was performed for 5 hours in a humidified incubator at 37° C. and 5% $CO_2$. Then, the plate was taken out of the incubator and left to stand for 10 to 15 minutes at room temperature. Subsequently, 75 µl of Bio-Glo™ reagent was added per well and the plate was left to stand for 5 minutes. Then, measurement was performed using GLOMAX™ Multi+ multi-well plate reader. From the measurement results, it was found that T cell activation was caused by the bispecific antibody in all three types of cancer cells, and it was observed that the $EC_{50}$ value increased as the affinity of the antibody to CD3 decreased. The bispecific antibody produced using Irrelevant Ab and Hu38 did not induce T cell activity (FIG. 5).

The invention claimed is:

1. A bispecific antibody, comprising:
    a first domain that specifically binds to GPNMB (glycoprotein non-metastatic melanoma protein B); and
    a second domain that specifically binds to CD3 (cluster of differentiation 3),
    wherein the first domain comprises
    a heavy chain variable region (VH) that comprises
        H-CDR1 of the amino acid sequence of SEQ ID NO: 1, 7, 8, 9, 10, or 11;
        H-CDR2 of the amino acid sequence of SEQ ID NO: 2; and
        H-CDR3 of the amino acid sequence of SEQ ID NO: 3; and
    a light chain variable region (VL) that comprises
        L-CDR1 of the amino acid sequence of SEQ ID NO: 4;
        L-CDR2 of the amino acid sequence of SEQ ID NO: 5 or 12; and
        L-CDR3 of the amino acid sequence of SEQ ID NO: 6.

2. The bispecific antibody of claim 1, wherein the heavy chain variable region and the light chain variable region of the first domain are linked to each other through a linker.

3. The bispecific antibody of claim 2, wherein the first domain comprises any one amino acid sequence selected from the group consisting of SEQ ID NOs: 19 to 25.

4. The bispecific antibody of claim 1, wherein the second domain comprises
    a heavy chain variable region (VH) that comprises
        H-CDR1 of the amino acid sequence of SEQ ID NO: 13; H-CDR2 of the amino acid sequence of SEQ ID NO: 14; and H-CDR3 of the amino acid sequence of SEQ ID NO: 15; and
    a light chain variable region (VL) that comprises L-CDR1 of the amino acid sequence of SEQ ID NO: 16; L-CDR2 of the amino acid sequence of SEQ ID NO: 17; and L-CDR3 of the amino acid sequence of SEQ ID NO: 18.

5. The anti-GPNMB/anti-CD3 bispecific antibody of claim 4, wherein the heavy chain variable region and the light chain variable region of the second domain are linked to each other through a linker.

6. The bispecific antibody of claim 5, wherein the second domain comprises the amino acid sequence of SEQ ID NO: 49 or SEQ ID NO: 51.

7. The bispecific antibody of claim 1, wherein the first domain and/or the second domain further comprises an Fc region.

8. The bispecific antibody of claim 7, wherein the Fc region of the first domain and/or the Fc region of the second domain is derived from the heavy chain constant region (CH) of IgG1, IgG2, IgG3, or IgG4.

9. The bispecific antibody of claim 7, wherein one of the Fc regions in the first domain and the second domain has a knob structure, and the other has a hole structure.

10. The bispecific antibody of claim 7, wherein the Fc region of the first domain comprises the amino acid sequence of SEQ ID NO: 47 or 48.

11. The bispecific antibody of claim 7, wherein the Fc region of the second domain comprises the amino acid sequence of SEQ ID NO: 48 or 47.

12. The bispecific antibody of claim 1, wherein the first domain comprises the amino acid sequence of SEQ ID NO: 34 or 35.

13. The bispecific antibody of claim 1, wherein the second domain comprises the amino acid sequence of SEQ ID NO: 36, 40, or 41.

14. The bispecific antibody of claim 1, wherein the bispecific antibody specifically binds to T cells and GPNMB-expressing cancer cells.

15. A polynucleotide selected from the following:
    (a) a polynucleotide encoding the first domain of claim 1,
    (b) a polynucleotide encoding the second domain of claim 1,
    (c) a polynucleotide encoding the first domain and the second domain of claim 1, or
    (d) a combination of (a) and (b).

16. An expression vector selected from
    (a') an expression vector loaded with the polynucleotide (a) of claim 15,
    (b') an expression vector loaded with the polynucleotide (b) of claim 15, (c') an expression vector loaded with the polynucleotide (c) of claim 15, or (d') a combination of (a') and (b').

17. A host cell, transformed with the expression vector of claim 16.

18. A method for producing an anti-GPNMB/anti-CD3 bispecific antibody, comprising steps of:

expressing the expression vector (c') or (d') of claim 16 in a culture; and isolating the anti-GPNMB/anti-CD3 antibody from the culture.

19. A pharmaceutical composition comprising the bispecific antibody of claim 1 and a pharmaceutically acceptable carrier.

20. A method for treating cancer in a subject, comprising administering, to the subject, an effective amount of the pharmaceutical composition of claim 19.

21. The method of claim 20, wherein the cancer expresses GPNMB.

22. The method of claim 21, wherein the cancer is one or more selected from the group consisting of colorectal cancer, lung cancer, brain cancer, pancreatic cancer, ovarian cancer, breast cancer, prostate cancer, liver cancer, thyroid cancer, head and neck cancer, gastric cancer, bladder cancer, non-Hodgkin's lymphoma, skin cancer, melanoma, leukemia, neuroblastoma, and glioblastoma.

23. The method of claim 20, wherein the first domain of the anti-GPNMB/anti-CD3 bispecific antibody comprises the amino acid sequence of SEQ ID NO: 34 or 35.

24. The method of claim 20, wherein the second domain of the anti-GPNMB/anti-CD3 bispecific antibody comprises the amino acid sequence of SEQ ID NO: 36, 40, or 41.

* * * * *

SEQUENCE LISTING

```
<160> NUMBER OF SEQ ID NOS: 61

<210> SEQ ID NO 1
<211> LENGTH: 10
<212> TYPE: PRT
<213> ORGANISM: Artificial Sequence
<220> FEATURE:
<223> OTHER INFORMATION: H-CDR1 of anti-GPNMB antibody

<400> SEQUENCE: 1

Gly Phe Thr Phe Ser Asn Tyr Ala Met Ser
1               5                   10

<210> SEQ ID NO 2
<211> LENGTH: 9
<212> TYPE: PRT
<213> ORGANISM: Artificial Sequence
<220> FEATURE:
<223> OTHER INFORMATION: H-CDR2 of anti-GPNMB antibody

<400> SEQUENCE: 2

Ser Ile Ser His Ser Gly Gly Ser Lys
1               5

<210> SEQ ID NO 3
<211> LENGTH: 7
<212> TYPE: PRT
<213> ORGANISM: Artificial Sequence
<220> FEATURE:
<223> OTHER INFORMATION: H-CDR3 of anti-GPNMB antibody

<400> SEQUENCE: 3

Lys Trp Ser Thr Phe Asp Tyr
1               5

<210> SEQ ID NO 4
<211> LENGTH: 10
<212> TYPE: PRT
<213> ORGANISM: Artificial Sequence
<220> FEATURE:
<223> OTHER INFORMATION: L-CDR1 of anti-GPNMB antibody
```

```
<400> SEQUENCE: 4

Ser Ser Asn Ile Gly Asn Asn Tyr Val Ser
1               5                   10

<210> SEQ ID NO 5
<211> LENGTH: 7
<212> TYPE: PRT
<213> ORGANISM: Artificial Sequence
<220> FEATURE:
<223> OTHER INFORMATION: L-CDR2 of anti-GPNMB antibody

<400> SEQUENCE: 5

Ala Asp Ser Gln Arg Pro Ser
1               5

<210> SEQ ID NO 6
<211> LENGTH: 11
<212> TYPE: PRT
<213> ORGANISM: Artificial Sequence
<220> FEATURE:
<223> OTHER INFORMATION: L-CDR3 of anti-GPNMB antibody

<400> SEQUENCE: 6

Gly Ala Trp Asp Ser Ser Leu Asn Ala Tyr Val
1               5                   10

<210> SEQ ID NO 7
<211> LENGTH: 10
<212> TYPE: PRT
<213> ORGANISM: Artificial Sequence
<220> FEATURE:
<223> OTHER INFORMATION: H-CDR1 of anti-GPNMB antibody

<400> SEQUENCE: 7

Gly Phe Thr Phe Arg Lys Leu Asn Met Ser
1               5                   10

<210> SEQ ID NO 8
<211> LENGTH: 10
<212> TYPE: PRT
<213> ORGANISM: Artificial Sequence
<220> FEATURE:
<223> OTHER INFORMATION: H-CDR1 of anti-GPNMB antibody

<400> SEQUENCE: 8

Gly Phe Thr Phe Arg Ala Arg Pro Met Ser
1               5                   10

<210> SEQ ID NO 9
<211> LENGTH: 10
<212> TYPE: PRT
<213> ORGANISM: Artificial Sequence
<220> FEATURE:
<223> OTHER INFORMATION: H-CDR1 of anti-GPNMB antibody

<400> SEQUENCE: 9

Gly Phe Thr Phe Gln Arg Tyr Pro Met Ser
1               5                   10

<210> SEQ ID NO 10
<211> LENGTH: 10
<212> TYPE: PRT
<213> ORGANISM: Artificial Sequence
<220> FEATURE:
<223> OTHER INFORMATION: H-CDR1 of anti-GPNMB antibody

<400> SEQUENCE: 10
```

```
Gly Phe Thr Phe Ile Arg Arg Pro Met Ser
1               5                   10

<210> SEQ ID NO 11
<211> LENGTH: 10
<212> TYPE: PRT
<213> ORGANISM: Artificial Sequence
<220> FEATURE:
<223> OTHER INFORMATION: H-CDR1 of anti-GPNMB antibody

<400> SEQUENCE: 11

Gly Phe Thr Phe Ala Ala Arg Pro Met Ser
1               5                   10

<210> SEQ ID NO 12
<211> LENGTH: 6
<212> TYPE: PRT
<213> ORGANISM: Artificial Sequence
<220> FEATURE:
<223> OTHER INFORMATION: L-CDR2 of anti-GPNMB antibody

<400> SEQUENCE: 12

Asp Thr Pro Leu Arg Pro
1               5

<210> SEQ ID NO 13
<211> LENGTH: 6
<212> TYPE: PRT
<213> ORGANISM: Artificial Sequence
<220> FEATURE:
<223> OTHER INFORMATION: H-CDR1 of anti-CD3 antibody

<400> SEQUENCE: 13

Asn Thr Tyr Ala Met Asn
1               5

<210> SEQ ID NO 14
<211> LENGTH: 20
<212> TYPE: PRT
<213> ORGANISM: Artificial Sequence
<220> FEATURE:
<223> OTHER INFORMATION: H-CDR2 of anti-CD3 antibody

<400> SEQUENCE: 14

Gly Arg Ile Arg Ser Lys Tyr Asn Asn Tyr Ala Thr Tyr Tyr Ala Asp
1               5                   10                  15

Ser Val Lys Asp
            20

<210> SEQ ID NO 15
<211> LENGTH: 14
<212> TYPE: PRT
<213> ORGANISM: Artificial Sequence
<220> FEATURE:
<223> OTHER INFORMATION: H-CDR3 of anti-CD3 antibody

<400> SEQUENCE: 15

His Gly Asn Phe Gly Asn Ser Tyr Val Ser Trp Phe Ala Tyr
1               5                   10

<210> SEQ ID NO 16
<211> LENGTH: 14
<212> TYPE: PRT
<213> ORGANISM: Artificial Sequence
<220> FEATURE:
<223> OTHER INFORMATION: L-CDR1 of anti-CD3 antibody
```

```
<400> SEQUENCE: 16

Arg Ser Ser Thr Gly Ala Val Thr Thr Ser Asn Tyr Ala Asn
1               5                   10

<210> SEQ ID NO 17
<211> LENGTH: 7
<212> TYPE: PRT
<213> ORGANISM: Artificial Sequence
<220> FEATURE:
<223> OTHER INFORMATION: L-CDR2 of anti-CD3 antibody

<400> SEQUENCE: 17

Gly Thr Asn Lys Arg Ala Pro
1               5

<210> SEQ ID NO 18
<211> LENGTH: 9
<212> TYPE: PRT
<213> ORGANISM: Artificial Sequence
<220> FEATURE:
<223> OTHER INFORMATION: L-CDR3 of anti-CD3 antibody

<400> SEQUENCE: 18

Ala Leu Trp Tyr Ser Asn Leu Trp Val
1               5

<210> SEQ ID NO 19
<211> LENGTH: 242
<212> TYPE: PRT
<213> ORGANISM: Artificial Sequence
<220> FEATURE:
<223> OTHER INFORMATION: scFv of anti-GPNMB antibody(GPNMB1)

<400> SEQUENCE: 19

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Ser Trp Val Arg Gln Ala Pro Gly Lys Gly Leu Glu Trp Val
        35                  40                  45

Ser Ser Ile Ser His Ser Gly Gly Ser Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Lys Trp Ser Thr Phe Asp Tyr Trp Gly Gln Gly Thr Leu Val
            100                 105                 110

Thr Val Ser Ser Gly Gly Gly Gly Ser Gly Gly Gly Gly Ser Gly Gly
        115                 120                 125

Gly Gly Ser Gln Ser Val Leu Thr Gln Pro Ser Ala Ser Gly Thr
    130                 135                 140

Pro Gly Gln Arg Val Thr Ile Ser Cys Ser Gly Ser Ser Ser Asn Ile
145                 150                 155                 160

Gly Asn Asn Tyr Val Ser Trp Tyr Gln Gln Leu Pro Gly Thr Ala Pro
                165                 170                 175

Lys Leu Leu Ile Tyr Ala Asp Ser Gln Arg Pro Ser Gly Val Pro Asp
            180                 185                 190

Arg Phe Ser Gly Ser Lys Ser Gly Thr Ser Ala Ser Leu Ala Ile Ser
```

```
                195                 200                 205
Gly Leu Arg Ser Glu Asp Glu Ala Asp Tyr Tyr Cys Gly Ala Trp Asp
            210                 215                 220

Ser Ser Leu Asn Ala Tyr Val Phe Gly Gly Gly Thr Lys Leu Thr Val
225                 230                 235                 240

Leu Gly

<210> SEQ ID NO 20
<211> LENGTH: 242
<212> TYPE: PRT
<213> ORGANISM: Artificial Sequence
<220> FEATURE:
<223> OTHER INFORMATION: scFv of anti-GPNMB antibody(GPNMB2)

<400> SEQUENCE: 20

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Arg Lys Leu
            20                  25                  30

Asn Met Ser Trp Val Arg Gln Ala Pro Gly Lys Gly Leu Glu Trp Val
        35                  40                  45

Ser Ser Ile Ser His Ser Gly Gly Ser Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Lys Trp Ser Thr Phe Asp Tyr Trp Gly Gln Gly Thr Leu Val
            100                 105                 110

Thr Val Ser Ser Gly Gly Gly Gly Ser Gly Gly Gly Gly Ser Gly Gly
        115                 120                 125

Gly Gly Ser Gln Ser Val Leu Thr Gln Pro Pro Ser Ala Ser Gly Thr
    130                 135                 140

Pro Gly Gln Arg Val Thr Ile Ser Cys Ser Gly Ser Ser Ser Asn Ile
145                 150                 155                 160

Gly Asn Asn Tyr Val Ser Trp Tyr Gln Gln Leu Pro Gly Thr Ala Pro
                165                 170                 175

Lys Leu Leu Ile Tyr Ala Asp Ser Gln Arg Pro Ser Gly Val Pro Asp
            180                 185                 190

Arg Phe Ser Gly Ser Lys Ser Gly Thr Ser Ala Ser Leu Ala Ile Ser
        195                 200                 205

Gly Leu Arg Ser Glu Asp Glu Ala Asp Tyr Tyr Cys Gly Ala Trp Asp
    210                 215                 220

Ser Ser Leu Asn Ala Tyr Val Phe Gly Gly Gly Thr Lys Leu Thr Val
225                 230                 235                 240

Leu Gly

<210> SEQ ID NO 21
<211> LENGTH: 242
<212> TYPE: PRT
<213> ORGANISM: Artificial Sequence
<220> FEATURE:
<223> OTHER INFORMATION: scFv of anti-GPNMB antibody(GPNMB3)

<400> SEQUENCE: 21

Glu Val Gln Leu Leu Glu Ser Gly Gly Gly Leu Val Gln Pro Gly Gly
1               5                   10                  15
```

```
Ser Leu Arg Leu Ser Cys Ala Ala Ser Gly Phe Thr Phe Arg Ala Arg
             20                  25                  30

Pro Met Ser Trp Val Arg Gln Ala Pro Gly Lys Gly Leu Glu Trp Val
         35                  40                  45

Ser Ser Ile Ser His Ser Gly Gly Ser Lys Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Lys Trp Ser Thr Phe Asp Tyr Trp Gly Gln Gly Thr Leu Val
             100                 105                 110

Thr Val Ser Ser Gly Gly Gly Gly Ser Gly Gly Gly Gly Ser Gly Gly
         115                 120                 125

Gly Gly Ser Gln Ser Val Leu Thr Gln Pro Pro Ser Ala Ser Gly Thr
             130                 135                 140

Pro Gly Gln Arg Val Thr Ile Ser Cys Ser Gly Ser Ser Ser Asn Ile
145                 150                 155                 160

Gly Asn Asn Tyr Val Ser Trp Tyr Gln Gln Leu Pro Gly Thr Ala Pro
                 165                 170                 175

Lys Leu Leu Ile Tyr Ala Asp Ser Gln Arg Pro Ser Gly Val Pro Asp
             180                 185                 190

Arg Phe Ser Gly Ser Lys Ser Gly Thr Ser Ala Ser Leu Ala Ile Ser
         195                 200                 205

Gly Leu Arg Ser Glu Asp Glu Ala Asp Tyr Tyr Cys Gly Ala Trp Asp
     210                 215                 220

Ser Ser Leu Asn Ala Tyr Val Phe Gly Gly Gly Thr Lys Leu Thr Val
225                 230                 235                 240

Leu Gly

<210> SEQ ID NO 22
<211> LENGTH: 242
<212> TYPE: PRT
<213> ORGANISM: Artificial Sequence
<220> FEATURE:
<223> OTHER INFORMATION: scFv of anti-GPNMB antibody(GPNMB4)

<400> SEQUENCE: 22

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Gln Arg Tyr
             20                  25                  30

Pro Met Ser Trp Val Arg Gln Ala Pro Gly Lys Gly Leu Glu Trp Val
         35                  40                  45

Ser Ser Ile Ser His Ser Gly Gly Ser Lys Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Lys Trp Ser Thr Phe Asp Tyr Trp Gly Gln Gly Thr Leu Val
             100                 105                 110

Thr Val Ser Ser Gly Gly Gly Gly Ser Gly Gly Gly Gly Ser Gly Gly
         115                 120                 125
```

Gly Gly Ser Gln Ser Val Leu Thr Gln Pro Pro Ser Ala Ser Gly Thr
130                 135                 140

Pro Gly Gln Arg Val Thr Ile Ser Cys Ser Gly Ser Ser Ser Asn Ile
145                 150                 155                 160

Gly Asn Asn Tyr Val Ser Trp Tyr Gln Gln Leu Pro Gly Thr Ala Pro
                165                 170                 175

Lys Leu Leu Ile Tyr Ala Asp Ser Gln Arg Pro Ser Gly Val Pro Asp
                180                 185                 190

Arg Phe Ser Gly Ser Lys Ser Gly Thr Ser Ala Ser Leu Ala Ile Ser
        195                 200                 205

Gly Leu Arg Ser Glu Asp Glu Ala Asp Tyr Tyr Cys Gly Ala Trp Asp
210                 215                 220

Ser Ser Leu Asn Ala Tyr Val Phe Gly Gly Gly Thr Lys Leu Thr Val
225                 230                 235                 240

Leu Gly

<210> SEQ ID NO 23
<211> LENGTH: 242
<212> TYPE: PRT
<213> ORGANISM: Artificial Sequence
<220> FEATURE:
<223> OTHER INFORMATION: scFv of anti-GPNMB antibody(GPNMB5)

<400> SEQUENCE: 23

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ile Arg Arg
                20                  25                  30

Pro Met Ser Trp Val Arg Gln Ala Pro Gly Lys Gly Leu Glu Trp Val
            35                  40                  45

Ser Ser Ile Ser His Ser Gly Ser Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Lys Trp Ser Thr Phe Asp Tyr Trp Gly Gln Gly Thr Leu Val
            100                 105                 110

Thr Val Ser Ser Gly Gly Gly Gly Ser Gly Gly Gly Gly Ser Gly Gly
        115                 120                 125

Gly Gly Ser Gln Ser Val Leu Thr Gln Pro Pro Ser Ala Ser Gly Thr
130                 135                 140

Pro Gly Gln Arg Val Thr Ile Ser Cys Ser Gly Ser Ser Ser Asn Ile
145                 150                 155                 160

Gly Asn Asn Tyr Val Ser Trp Tyr Gln Gln Leu Pro Gly Thr Ala Pro
                165                 170                 175

Lys Leu Leu Ile Tyr Ala Asp Ser Gln Arg Pro Ser Gly Val Pro Asp
                180                 185                 190

Arg Phe Ser Gly Ser Lys Ser Gly Thr Ser Ala Ser Leu Ala Ile Ser
        195                 200                 205

Gly Leu Arg Ser Glu Asp Glu Ala Asp Tyr Tyr Cys Gly Ala Trp Asp
210                 215                 220

Ser Ser Leu Asn Ala Tyr Val Phe Gly Gly Gly Thr Lys Leu Thr Val
225                 230                 235                 240

Leu Gly

<210> SEQ ID NO 24
<211> LENGTH: 242
<212> TYPE: PRT
<213> ORGANISM: Artificial Sequence
<220> FEATURE:
<223> OTHER INFORMATION: scFv of anti-GPNMB antibody(GPNMB6)

<400> SEQUENCE: 24

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ala Ala Arg
            20                  25                  30

Pro Met Ser Trp Val Arg Gln Ala Pro Gly Lys Gly Leu Glu Trp Val
        35                  40                  45

Ser Ser Ile Ser His Ser Gly Gly Ser Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Lys Trp Ser Thr Phe Asp Tyr Trp Gly Gln Gly Thr Leu Val
            100                 105                 110

Thr Val Ser Ser Gly Gly Gly Gly Ser Gly Gly Gly Gly Ser Gly Gly
        115                 120                 125

Gly Gly Ser Gln Ser Val Leu Thr Gln Pro Ser Ala Ser Gly Thr
    130                 135                 140

Pro Gly Gln Arg Val Thr Ile Ser Cys Ser Gly Ser Ser Ser Asn Ile
145                 150                 155                 160

Gly Asn Asn Tyr Val Ser Trp Tyr Gln Gln Leu Pro Gly Thr Ala Pro
                165                 170                 175

Lys Leu Leu Ile Tyr Ala Asp Ser Gln Arg Pro Ser Gly Val Pro Asp
            180                 185                 190

Arg Phe Ser Gly Ser Lys Ser Gly Thr Ser Ala Ser Leu Ala Ile Ser
        195                 200                 205

Gly Leu Arg Ser Glu Asp Glu Ala Asp Tyr Tyr Cys Gly Ala Trp Asp
    210                 215                 220

Ser Ser Leu Asn Ala Tyr Val Phe Gly Gly Thr Lys Leu Thr Val
225                 230                 235                 240

Leu Gly

<210> SEQ ID NO 25
<211> LENGTH: 242
<212> TYPE: PRT
<213> ORGANISM: Artificial Sequence
<220> FEATURE:
<223> OTHER INFORMATION: scFv of anti-GPNMB antibody(GPNMB7)

<400> SEQUENCE: 25

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Ser Trp Val Arg Gln Ala Pro Gly Lys Gly Leu Glu Trp Val
        35                  40                  45

Ser Ser Ile Ser His Ser Gly Gly Ser Lys Tyr Tyr Ala Asp Ser Val
    50                  55                  60

```
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Lys Trp Ser Thr Phe Asp Tyr Trp Gly Gln Gly Thr Leu Val
            100                 105                 110

Thr Val Ser Ser Gly Gly Gly Ser Gly Gly Gly Ser Gly Gly
        115                 120                 125

Gly Gly Ser Gln Ser Val Leu Thr Gln Pro Pro Ser Ala Ser Gly Thr
        130                 135                 140

Pro Gly Gln Arg Val Thr Ile Ser Cys Ser Gly Ser Ser Ser Asn Ile
145                 150                 155                 160

Gly Asn Asn Tyr Val Ser Trp Tyr Gln Gln Leu Pro Gly Thr Ala Pro
                165                 170                 175

Lys Leu Leu Ile Tyr Asp Thr Pro Leu Arg Pro Ser Gly Val Pro Asp
                180                 185                 190

Arg Phe Ser Gly Ser Lys Ser Gly Thr Ser Ala Ser Leu Ala Ile Ser
            195                 200                 205

Gly Leu Arg Ser Glu Asp Glu Ala Asp Tyr Tyr Cys Gly Ala Trp Asp
        210                 215                 220

Ser Ser Leu Asn Ala Tyr Val Phe Gly Gly Asp Thr Lys Leu Thr Val
225                 230                 235                 240

Leu Gly
```

```
<210> SEQ ID NO 26
<211> LENGTH: 116
<212> TYPE: PRT
<213> ORGANISM: Artificial Sequence
<220> FEATURE:
<223> OTHER INFORMATION: VH sequence of anti-GPNMB antibody(GPNMB1,
      GPNMB7)

<400> SEQUENCE: 26

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Ser Asn Tyr
                 20                  25                  30

Ala Met Ser Trp Val Arg Gln Ala Pro Gly Lys Gly Leu Glu Trp Val
             35                  40                  45

Ser Ser Ile Ser His Ser Gly Gly Ser Lys Tyr Tyr Ala Asp Ser Val
         50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Lys Trp Ser Thr Phe Asp Tyr Trp Gly Gln Gly Thr Leu Val
            100                 105                 110

Thr Val Ser Ser
        115
```

```
<210> SEQ ID NO 27
<211> LENGTH: 116
<212> TYPE: PRT
<213> ORGANISM: Artificial Sequence
<220> FEATURE:
<223> OTHER INFORMATION: VH sequence of anti-GPNMB antibody(GPNMB2)
```

```
<400> SEQUENCE: 27

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Arg Lys Leu
            20                  25                  30

Asn Met Ser Trp Val Arg Gln Ala Pro Gly Lys Gly Leu Glu Trp Val
        35                  40                  45

Ser Ser Ile Ser His Ser Gly Gly Ser Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Arg Lys Trp Ser Thr Phe Asp Tyr Trp Gly Gln Gly Thr Leu Val
            100                 105                 110

Thr Val Ser Ser
        115

<210> SEQ ID NO 28
<211> LENGTH: 116
<212> TYPE: PRT
<213> ORGANISM: Artificial Sequence
<220> FEATURE:
<223> OTHER INFORMATION: VH sequence of anti-GPNMB antibody(GPNMB3)

<400> SEQUENCE: 28

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Arg Ala Arg
            20                  25                  30

Pro Met Ser Trp Val Arg Gln Ala Pro Gly Lys Gly Leu Glu Trp Val
        35                  40                  45

Ser Ser Ile Ser His Ser Gly Gly Ser Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Arg Lys Trp Ser Thr Phe Asp Tyr Trp Gly Gln Gly Thr Leu Val
            100                 105                 110

Thr Val Ser Ser
        115

<210> SEQ ID NO 29
<211> LENGTH: 116
<212> TYPE: PRT
<213> ORGANISM: Artificial Sequence
<220> FEATURE:
<223> OTHER INFORMATION: VH sequence of anti-GPNMB antibody(GPNMB4)

<400> SEQUENCE: 29

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Gln Arg Tyr
            20                  25                  30

Pro Met Ser Trp Val Arg Gln Ala Pro Gly Lys Gly Leu Glu Trp Val
        35                  40                  45
```

Ser Ser Ile Ser His Ser Gly Gly Ser Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Lys Trp Ser Thr Phe Asp Tyr Trp Gly Gln Gly Thr Leu Val
            100                 105                 110

Thr Val Ser Ser
        115

<210> SEQ ID NO 30
<211> LENGTH: 116
<212> TYPE: PRT
<213> ORGANISM: Artificial Sequence
<220> FEATURE:
<223> OTHER INFORMATION: VH sequence of anti-GPNMB antibody(GPNMB5)

<400> SEQUENCE: 30

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ile Arg Arg
            20                  25                  30

Pro Met Ser Trp Val Arg Gln Ala Pro Gly Lys Gly Leu Glu Trp Val
        35                  40                  45

Ser Ser Ile Ser His Ser Gly Gly Ser Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Lys Trp Ser Thr Phe Asp Tyr Trp Gly Gln Gly Thr Leu Val
            100                 105                 110

Thr Val Ser Ser
        115

<210> SEQ ID NO 31
<211> LENGTH: 116
<212> TYPE: PRT
<213> ORGANISM: Artificial Sequence
<220> FEATURE:
<223> OTHER INFORMATION: VH sequence of anti-GPNMB antibody(GPNMB6)

<400> SEQUENCE: 31

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ala Ala Arg
            20                  25                  30

Pro Met Ser Trp Val Arg Gln Ala Pro Gly Lys Gly Leu Glu Trp Val
        35                  40                  45

Ser Ser Ile Ser His Ser Gly Gly Ser Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Lys Trp Ser Thr Phe Asp Tyr Trp Gly Gln Gly Thr Leu Val
            100                 105                 110

```
Thr Val Ser Ser
        115

<210> SEQ ID NO 32
<211> LENGTH: 111
<212> TYPE: PRT
<213> ORGANISM: Artificial Sequence
<220> FEATURE:
<223> OTHER INFORMATION: VL sequence of anti-GPNMB antibody

<400> SEQUENCE: 32

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Asn Asn
            20                  25                  30

Tyr Val Ser Trp Tyr Gln Gln Leu Pro Gly Thr Ala Pro Lys Leu Leu
        35                  40                  45

Ile Tyr Ala Asp Ser Gln Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Ala Trp Asp Ser Ser Leu
                85                  90                  95

Asn Ala Tyr Val Phe Gly Gly Gly Thr Lys Leu Thr Val Leu Gly
            100                 105                 110

<210> SEQ ID NO 33
<211> LENGTH: 111
<212> TYPE: PRT
<213> ORGANISM: Artificial Sequence
<220> FEATURE:
<223> OTHER INFORMATION: VL sequence of anti-GPNMB antibody(GPNMB7)

<400> SEQUENCE: 33

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Asn Asn
            20                  25                  30

Tyr Val Ser Trp Tyr Gln Gln Leu Pro Gly Thr Ala Pro Lys Leu Leu
        35                  40                  45

Ile Tyr Asp Thr Pro Leu Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Ala Trp Asp Ser Ser Leu
                85                  90                  95

Asn Ala Tyr Val Phe Gly Gly Asp Thr Lys Leu Thr Val Leu Gly
            100                 105                 110

<210> SEQ ID NO 34
<211> LENGTH: 714
<212> TYPE: PRT
<213> ORGANISM: Artificial Sequence
<220> FEATURE:
<223> OTHER INFORMATION: anti-GPNMB1-VL-CL-linker-VH-CH (Knob vector)

<400> SEQUENCE: 34

Met Asp Ser Gln Ala Gln Val Leu Met Leu Leu Leu Leu Trp Val Ser
1               5                   10                  15
```

-continued

```
Gly Thr Cys Gly Gln Ser Val Leu Thr Gln Pro Ser Ala Ser Gly
             20                  25                  30

Thr Pro Gly Gln Arg Val Thr Ile Ser Cys Ser Gly Ser Ser Asn
         35                  40                  45

Ile Gly Asn Asn Tyr Val Ser Trp Tyr Gln Gln Leu Pro Gly Thr Ala
    50                  55                  60

Pro Lys Leu Leu Ile Tyr Ala Asp Ser Gln Arg Pro Ser Gly Val Pro
65                  70                  75                  80

Asp Arg Phe Ser Gly Ser Lys Ser Gly Thr Ser Ala Ser Leu Ala Ile
                85                  90                  95

Ser Gly Leu Arg Ser Glu Asp Glu Ala Asp Tyr Tyr Cys Gly Ala Trp
            100                 105                 110

Asp Ser Ser Leu Asn Ala Tyr Val Phe Gly Gly Gly Thr Lys Leu Thr
        115                 120                 125

Val Leu Gly Gln Pro Lys Ala Asn Pro Thr Val Thr Leu Phe Pro Pro
    130                 135                 140

Ser Ser Glu Glu Leu Gln Ala Asn Lys Ala Thr Leu Val Cys Leu Ile
145                 150                 155                 160

Ser Asp Phe Tyr Pro Gly Ala Val Thr Val Ala Trp Lys Ala Asp Gly
                165                 170                 175

Ser Pro Val Lys Ala Gly Val Glu Thr Thr Lys Pro Ser Lys Gln Ser
            180                 185                 190

Asn Asn Lys Tyr Ala Ala Ser Ser Tyr Leu Ser Leu Thr Pro Glu Gln
        195                 200                 205

Trp Lys Ser His Arg Ser Tyr Ser Cys Gln Val Thr His Glu Gly Ser
    210                 215                 220

Thr Val Glu Lys Thr Val Ala Pro Thr Glu Cys Ser Gly Gly Gly Ser
225                 230                 235                 240

Gly Gly Gly Ser Glu Gly Gly Ser Glu Gly Gly Ser Glu Gly
                245                 250                 255

Gly Gly Ser Glu Gly Gly Ser Gly Gly Ser Gly Glu Val Gln
            260                 265                 270

Leu Leu Glu Ser Gly Gly Gly Leu Val Gln Pro Gly Gly Ser Leu Arg
        275                 280                 285

Leu Ser Cys Ala Ala Ser Gly Phe Thr Phe Ser Asn Tyr Ala Met Ser
    290                 295                 300

Trp Val Arg Gln Ala Pro Gly Lys Gly Leu Glu Trp Val Ser Ser Ile
305                 310                 315                 320

Ser His Ser Gly Gly Ser Lys Tyr Tyr Ala Asp Ser Val Lys Gly Arg
                325                 330                 335

Phe Thr Ile Ser Arg Asp Asn Ser Lys Asn Thr Leu Tyr Leu Gln Met
            340                 345                 350

Asn Ser Leu Arg Ala Glu Asp Thr Ala Val Tyr Tyr Cys Ala Arg Lys
        355                 360                 365

Trp Ser Thr Phe Asp Tyr Trp Gly Gln Gly Thr Leu Val Thr Val Ser
    370                 375                 380

Ser Ala Ser Thr Lys Gly Pro Ser Val Phe Pro Leu Ala Pro Ser Ser
385                 390                 395                 400

Lys Ser Thr Ser Gly Gly Thr Ala Ala Leu Gly Cys Leu Val Lys Asp
                405                 410                 415

Tyr Phe Pro Glu Pro Val Thr Val Ser Trp Asn Ser Gly Ala Leu Thr
            420                 425                 430

Ser Gly Val His Thr Phe Pro Ala Val Leu Gln Ser Ser Gly Leu Tyr
```

```
                435                 440                 445
Ser Leu Ser Ser Val Val Thr Val Pro Ser Ser Leu Gly Thr Gln
        450                 455                 460

Thr Tyr Ile Cys Asn Val Asn His Lys Pro Ser Asn Thr Lys Val Asp
465                 470                 475                 480

Lys Lys Val Glu Pro Lys Ser Cys Asp Lys Thr His Thr Cys Pro Pro
                485                 490                 495

Cys Pro Ala Pro Glu Ala Ala Gly Gly Pro Ser Val Phe Leu Phe Pro
                500                 505                 510

Pro Lys Pro Lys Asp Thr Leu Met Ile Ser Arg Thr Pro Glu Val Thr
            515                 520                 525

Cys Val Val Val Asp Val Ser His Glu Asp Pro Glu Val Lys Phe Asn
530                 535                 540

Trp Tyr Val Asp Gly Val Glu Val His Asn Ala Lys Thr Lys Pro Arg
545                 550                 555                 560

Glu Glu Gln Tyr Asn Ser Thr Tyr Arg Val Val Ser Val Leu Thr Val
                565                 570                 575

Leu His Gln Asp Trp Leu Asn Gly Lys Glu Tyr Lys Cys Lys Val Ser
            580                 585                 590

Asn Lys Ala Leu Pro Ala Pro Ile Glu Lys Thr Ile Ser Lys Ala Lys
                595                 600                 605

Gly Gln Pro Arg Glu Pro Gln Val Cys Thr Leu Pro Pro Ser Arg Asp
610                 615                 620

Glu Leu Thr Glu Asn Gln Val Ser Leu Thr Cys Leu Val Lys Gly Phe
625                 630                 635                 640

Tyr Pro Ser Asp Ile Ala Val Glu Trp Glu Ser Asn Gly Gln Pro Glu
                645                 650                 655

Asn Asn Tyr Lys Thr Thr Pro Pro Val Leu Asp Ser Asp Gly Ser Phe
            660                 665                 670

Phe Leu Tyr Ser Trp Leu Thr Val Asp Lys Ser Arg Trp Gln Gln Gly
                675                 680                 685

Asn Val Phe Ser Cys Ser Val Met His Glu Ala Leu His Asn His Tyr
            690                 695                 700

Thr Gln Lys Ser Leu Ser Leu Ser Pro Gly
705                 710

<210> SEQ ID NO 35
<211> LENGTH: 714
<212> TYPE: PRT
<213> ORGANISM: Artificial Sequence
<220> FEATURE:
<223> OTHER INFORMATION: anti-GPNMB6-VL-CL-linker-VH-CH (Knob vector)

<400> SEQUENCE: 35

Met Asp Ser Gln Ala Gln Val Leu Met Leu Leu Leu Leu Trp Val Ser
1               5                   10                  15

Gly Thr Cys Gly Gln Ser Val Leu Thr Gln Pro Pro Ser Ala Ser Gly
            20                  25                  30

Thr Pro Gly Gln Arg Val Thr Ile Ser Cys Ser Gly Ser Ser Ser Asn
        35                  40                  45

Ile Gly Asn Asn Tyr Val Ser Trp Tyr Gln Gln Leu Pro Gly Thr Ala
    50                  55                  60

Pro Lys Leu Leu Ile Tyr Ala Asp Ser Gln Arg Pro Ser Gly Val Pro
65                  70                  75                  80

Asp Arg Phe Ser Gly Ser Lys Ser Gly Thr Ser Ala Ser Leu Ala Ile
```

```
                    85                  90                  95
Ser Gly Leu Arg Ser Glu Asp Glu Ala Asp Tyr Tyr Cys Gly Ala Trp
                100                 105                 110

Asp Ser Ser Leu Asn Ala Tyr Val Phe Gly Gly Gly Thr Lys Leu Thr
                115                 120                 125

Val Leu Gly Gln Pro Lys Ala Asn Pro Thr Val Thr Leu Phe Pro Pro
            130                 135                 140

Ser Ser Glu Glu Leu Gln Ala Asn Lys Ala Thr Leu Val Cys Leu Ile
145                 150                 155                 160

Ser Asp Phe Tyr Pro Gly Ala Val Thr Val Ala Trp Lys Ala Asp Gly
                165                 170                 175

Ser Pro Val Lys Ala Gly Val Glu Thr Thr Lys Pro Ser Lys Gln Ser
            180                 185                 190

Asn Asn Lys Tyr Ala Ala Ser Ser Tyr Leu Ser Leu Thr Pro Glu Gln
            195                 200                 205

Trp Lys Ser His Arg Ser Tyr Ser Cys Gln Val Thr His Glu Gly Ser
        210                 215                 220

Thr Val Glu Lys Thr Val Ala Pro Thr Glu Cys Ser Gly Gly Gly Ser
225                 230                 235                 240

Gly Gly Gly Ser Glu Gly Gly Ser Glu Gly Gly Ser Glu Gly
                245                 250                 255

Gly Gly Ser Glu Gly Gly Ser Gly Gly Ser Gly Glu Val Gln
            260                 265                 270

Leu Leu Glu Ser Gly Gly Gly Leu Val Gln Pro Gly Gly Ser Leu Arg
                275                 280                 285

Leu Ser Cys Ala Ala Ser Gly Phe Thr Phe Ala Ala Arg Pro Met Ser
        290                 295                 300

Trp Val Arg Gln Ala Pro Gly Lys Gly Leu Glu Trp Val Ser Ser Ile
305                 310                 315                 320

Ser His Ser Gly Gly Ser Lys Tyr Tyr Ala Asp Ser Val Lys Gly Arg
                325                 330                 335

Phe Thr Ile Ser Arg Asp Asn Ser Lys Asn Thr Leu Tyr Leu Gln Met
            340                 345                 350

Asn Ser Leu Arg Ala Glu Asp Thr Ala Val Tyr Tyr Cys Ala Arg Lys
            355                 360                 365

Trp Ser Thr Phe Asp Tyr Trp Gly Gln Gly Thr Leu Val Thr Val Ser
        370                 375                 380

Ser Ala Ser Thr Lys Gly Pro Ser Val Phe Pro Leu Ala Pro Ser Ser
385                 390                 395                 400

Lys Ser Thr Ser Gly Gly Thr Ala Ala Leu Gly Cys Leu Val Lys Asp
                405                 410                 415

Tyr Phe Pro Glu Pro Val Thr Val Ser Trp Asn Ser Gly Ala Leu Thr
            420                 425                 430

Ser Gly Val His Thr Phe Pro Ala Val Leu Gln Ser Ser Gly Leu Tyr
            435                 440                 445

Ser Leu Ser Ser Val Val Thr Val Pro Ser Ser Ser Leu Gly Thr Gln
450                 455                 460

Thr Tyr Ile Cys Asn Val Asn His Lys Pro Ser Asn Thr Lys Val Asp
465                 470                 475                 480

Lys Lys Val Glu Pro Lys Ser Cys Asp Lys Thr His Thr Cys Pro Pro
                485                 490                 495

Cys Pro Ala Pro Glu Ala Ala Gly Gly Pro Ser Val Phe Leu Phe Pro
            500                 505                 510
```

-continued

Pro Lys Pro Lys Asp Thr Leu Met Ile Ser Arg Thr Pro Glu Val Thr
        515                 520                 525

Cys Val Val Asp Val Ser His Glu Asp Pro Glu Val Lys Phe Asn
    530                 535                 540

Trp Tyr Val Asp Gly Val Glu Val His Asn Ala Lys Thr Lys Pro Arg
545                 550                 555                 560

Glu Glu Gln Tyr Asn Ser Thr Tyr Arg Val Val Ser Val Leu Thr Val
                565                 570                 575

Leu His Gln Asp Trp Leu Asn Gly Lys Glu Tyr Lys Cys Lys Val Ser
            580                 585                 590

Asn Lys Ala Leu Pro Ala Pro Ile Glu Lys Thr Ile Ser Lys Ala Lys
        595                 600                 605

Gly Gln Pro Arg Glu Pro Gln Val Cys Thr Leu Pro Pro Ser Arg Asp
    610                 615                 620

Glu Leu Thr Glu Asn Gln Val Ser Leu Thr Cys Leu Val Lys Gly Phe
625                 630                 635                 640

Tyr Pro Ser Asp Ile Ala Val Glu Trp Glu Ser Asn Gly Gln Pro Glu
                645                 650                 655

Asn Asn Tyr Lys Thr Thr Pro Pro Val Leu Asp Ser Asp Gly Ser Phe
            660                 665                 670

Phe Leu Tyr Ser Trp Leu Thr Val Asp Lys Ser Arg Trp Gln Gln Gly
        675                 680                 685

Asn Val Phe Ser Cys Ser Val Met His Glu Ala Leu His Asn His Tyr
    690                 695                 700

Thr Gln Lys Ser Leu Ser Leu Ser Pro Gly
705                 710

<210> SEQ ID NO 36
<211> LENGTH: 722
<212> TYPE: PRT
<213> ORGANISM: Artificial Sequence
<220> FEATURE:
<223> OTHER INFORMATION: anti-CD3(A15)-VL-CL-linker-VH-CH (Hole vector)

<400> SEQUENCE: 36

Met Asp Ser Gln Ala Gln Val Leu Met Leu Leu Leu Leu Trp Val Ser
1               5                   10                  15

Gly Thr Cys Gly Gln Ala Val Val Thr Gln Glu Pro Ser Leu Thr Val
            20                  25                  30

Ser Pro Gly Gly Thr Val Thr Leu Thr Cys Arg Ser Ser Thr Gly Ala
        35                  40                  45

Val Thr Thr Ser Asn Tyr Ala Asn Trp Val Gln Gln Lys Pro Gly Gln
    50                  55                  60

Ala Pro Arg Gly Leu Ile Gly Gly Thr Asn Lys Arg Ala Pro Trp Thr
65                  70                  75                  80

Pro Ala Arg Phe Ser Gly Ser Leu Leu Gly Gly Lys Ala Ala Leu Thr
                85                  90                  95

Leu Ser Gly Ala Gln Pro Glu Asp Glu Ala Glu Tyr Tyr Cys Ala Leu
            100                 105                 110

Trp Tyr Ser Asn Leu Trp Val Phe Gly Gly Gly Thr Lys Leu Thr Val
        115                 120                 125

Leu Gly Gln Pro Lys Ala Asn Pro Thr Val Thr Leu Phe Pro Pro Ser
    130                 135                 140

Ser Glu Glu Leu Gln Ala Asn Lys Ala Thr Leu Val Cys Leu Ile Ser
145                 150                 155                 160

```
Asp Phe Tyr Pro Gly Ala Val Thr Val Ala Trp Lys Ala Asp Gly Ser
            165                 170                 175

Pro Val Lys Ala Gly Val Glu Thr Thr Lys Pro Ser Lys Gln Ser Asn
        180                 185                 190

Asn Lys Tyr Ala Ala Ser Ser Tyr Leu Ser Leu Thr Pro Glu Gln Trp
            195                 200                 205

Lys Ser His Arg Ser Tyr Ser Cys Gln Val Thr His Glu Gly Ser Thr
        210                 215                 220

Val Glu Lys Thr Val Ala Pro Thr Glu Cys Ser Gly Gly Ser Gly
225                 230                 235                 240

Gly Gly Ser Glu Gly Gly Ser Glu Gly Gly Ser Glu Gly Gly
            245                 250                 255

Gly Ser Glu Gly Gly Gly Ser Gly Gly Gly Ser Gly Glu Val Gln Leu
        260                 265                 270

Val Glu Ser Gly Gly Gly Leu Val Gln Pro Gly Gly Ser Leu Lys Leu
275                 280                 285

Ser Cys Ala Ala Ser Gly Phe Thr Phe Asn Thr Tyr Ala Met Asn Trp
        290                 295                 300

Val Arg Gln Ala Ser Gly Lys Gly Leu Glu Trp Val Gly Arg Ile Arg
305                 310                 315                 320

Ser Lys Tyr Asn Asn Tyr Ala Thr Tyr Tyr Ala Asp Ser Val Lys Asp
            325                 330                 335

Arg Phe Thr Ile Ser Arg Asp Asp Ser Lys Asn Thr Ala Tyr Leu Gln
        340                 345                 350

Met Asn Ser Leu Lys Thr Glu Asp Thr Ala Val Tyr Tyr Cys Val Arg
            355                 360                 365

His Gly Asn Phe Gly Asn Ser Tyr Val Ser Trp Phe Ala Tyr Trp Gly
        370                 375                 380

Gln Gly Thr Leu Val Thr Val Ser Ser Ala Ser Thr Lys Gly Pro Ser
385                 390                 395                 400

Val Phe Pro Leu Ala Pro Ser Ser Lys Ser Thr Ser Gly Gly Thr Ala
            405                 410                 415

Ala Leu Gly Cys Leu Val Lys Asp Tyr Phe Pro Glu Pro Val Thr Val
        420                 425                 430

Ser Trp Asn Ser Gly Ala Leu Thr Ser Gly Val His Thr Phe Pro Ala
        435                 440                 445

Val Leu Gln Ser Ser Gly Leu Tyr Ser Leu Ser Ser Val Val Thr Val
        450                 455                 460

Pro Ser Ser Ser Leu Gly Thr Gln Thr Tyr Ile Cys Asn Val Asn His
465                 470                 475                 480

Lys Pro Ser Asn Thr Lys Val Asp Lys Lys Val Glu Pro Lys Ser Cys
            485                 490                 495

Asp Lys Thr His Thr Cys Pro Pro Cys Pro Ala Pro Glu Ala Ala Gly
        500                 505                 510

Gly Pro Ser Val Phe Leu Phe Pro Pro Lys Pro Lys Asp Thr Leu Met
        515                 520                 525

Ile Ser Arg Thr Pro Glu Val Thr Cys Val Val Asp Val Ser His
        530                 535                 540

Glu Asp Pro Glu Val Lys Phe Asn Trp Tyr Val Asp Gly Val Glu Val
545                 550                 555                 560

His Asn Ala Lys Thr Lys Pro Arg Glu Glu Gln Tyr Asn Ser Thr Tyr
            565                 570                 575
```

```
Arg Val Val Ser Val Leu Thr Val Leu His Gln Asp Trp Leu Asn Gly
            580                 585                 590

Lys Glu Tyr Lys Cys Lys Val Ser Asn Lys Ala Leu Pro Ala Pro Ile
        595                 600                 605

Glu Lys Thr Ile Ser Lys Ala Lys Gly Gln Pro Arg Glu Pro Arg Val
    610                 615                 620

Tyr Thr Leu Pro Pro Cys Arg Asp Glu Leu Thr Lys Asn Gln Val Ser
625                 630                 635                 640

Leu Thr Cys Leu Val Lys Gly Phe Tyr Pro Ser Asp Ile Ala Val Glu
            645                 650                 655

Trp Glu Ser Asn Gly Gln Pro Glu Asn Asn Tyr Lys Thr Thr Pro Pro
            660                 665                 670

Val Leu Val Ser Asp Gly Ser Phe Thr Leu Tyr Ser Lys Leu Thr Val
            675                 680                 685

Asp Lys Ser Arg Trp Gln Gln Gly Asn Val Phe Ser Cys Ser Val Met
        690                 695                 700

His Glu Ala Leu His Asn His Tyr Thr Gln Lys Ser Leu Ser Leu Ser
705                 710                 715                 720

Pro Gly

<210> SEQ ID NO 37
<211> LENGTH: 464
<212> TYPE: PRT
<213> ORGANISM: Artificial Sequence
<220> FEATURE:
<223> OTHER INFORMATION: Human GPNMB protein sequence (Lys23-Asn486):
      R&D systems 2550-AC

<400> SEQUENCE: 37

Lys Arg Phe His Asp Val Leu Gly Asn Glu Arg Pro Ser Ala Tyr Met
1               5                   10                  15

Arg Glu His Asn Gln Leu Asn Gly Trp Ser Ser Asp Glu Asn Asp Trp
            20                  25                  30

Asn Glu Lys Leu Tyr Pro Val Trp Lys Arg Gly Asp Met Arg Trp Lys
        35                  40                  45

Asn Ser Trp Lys Gly Gly Arg Val Gln Ala Val Leu Thr Ser Asp Ser
    50                  55                  60

Pro Ala Leu Val Gly Ser Asn Ile Thr Phe Ala Val Asn Leu Ile Phe
65                  70                  75                  80

Pro Arg Cys Gln Lys Glu Asp Ala Asn Gly Asn Ile Val Tyr Glu Lys
            85                  90                  95

Asn Cys Arg Asn Glu Ala Gly Leu Ser Ala Asp Pro Tyr Val Tyr Asn
            100                 105                 110

Trp Thr Ala Trp Ser Glu Asp Ser Asp Gly Glu Asn Gly Thr Gly Gln
        115                 120                 125

Ser His His Asn Val Phe Pro Asp Gly Lys Pro Phe Pro His His Pro
    130                 135                 140

Gly Trp Arg Arg Trp Asn Phe Ile Tyr Val Phe His Thr Leu Gly Gln
145                 150                 155                 160

Tyr Phe Gln Lys Leu Gly Arg Cys Ser Val Arg Val Ser Val Asn Thr
            165                 170                 175

Ala Asn Val Thr Leu Gly Pro Gln Leu Met Glu Val Thr Val Tyr Arg
            180                 185                 190

Arg His Gly Arg Ala Tyr Val Pro Ile Ala Gln Val Lys Asp Val Tyr
        195                 200                 205
```

```
Val Val Thr Asp Gln Ile Pro Val Phe Val Thr Met Phe Gln Lys Asn
            210                 215                 220

Asp Arg Asn Ser Ser Asp Glu Thr Phe Leu Lys Asp Leu Pro Ile Met
225                 230                 235                 240

Phe Asp Val Leu Ile His Asp Pro Ser His Phe Leu Asn Tyr Ser Thr
                    245                 250                 255

Ile Asn Tyr Lys Trp Ser Phe Gly Asp Asn Thr Gly Leu Phe Val Ser
                260                 265                 270

Thr Asn His Thr Val Asn His Thr Tyr Val Leu Asn Gly Thr Phe Ser
            275                 280                 285

Leu Asn Leu Thr Val Lys Ala Ala Pro Gly Pro Cys Pro Pro Pro
290                 295                 300

Pro Pro Pro Pro Arg Pro Ser Lys Pro Thr Pro Ser Leu Gly Pro Ala
305                 310                 315                 320

Gly Asp Asn Pro Leu Glu Leu Ser Arg Ile Pro Asp Glu Asn Cys Gln
                325                 330                 335

Ile Asn Arg Tyr Gly His Phe Gln Ala Thr Ile Thr Ile Val Glu Gly
                340                 345                 350

Ile Leu Glu Val Asn Ile Ile Gln Met Thr Asp Val Leu Met Pro Val
                355                 360                 365

Pro Trp Pro Glu Ser Ser Leu Ile Asp Phe Val Val Thr Cys Gln Gly
370                 375                 380

Ser Ile Pro Thr Glu Val Cys Thr Ile Ile Ser Asp Pro Thr Cys Glu
385                 390                 395                 400

Ile Thr Gln Asn Thr Val Cys Ser Pro Val Asp Val Asp Glu Met Cys
                405                 410                 415

Leu Leu Thr Val Arg Arg Thr Phe Asn Gly Ser Gly Thr Tyr Cys Val
                420                 425                 430

Asn Leu Thr Leu Gly Asp Asp Thr Ser Leu Ala Leu Thr Ser Thr Leu
                435                 440                 445

Ile Ser Val Pro Asp Arg Asp Pro Ala Ser Pro Leu Arg Met Ala Asn
                450                 455                 460

<210> SEQ ID NO 38
<211> LENGTH: 104
<212> TYPE: PRT
<213> ORGANISM: Artificial Sequence
<220> FEATURE:
<223> OTHER INFORMATION: Human CD3 protein (epsilon-delta) : Asp 23 -
      Asp 126

<400> SEQUENCE: 38

Asp Gly Asn Glu Glu Met Gly Gly Ile Thr Gln Thr Pro Tyr Lys Val
1               5                   10                  15

Ser Ile Ser Gly Thr Thr Val Ile Leu Thr Cys Pro Gln Tyr Pro Gly
            20                  25                  30

Ser Glu Ile Leu Trp Gln His Asn Asp Lys Asn Ile Gly Gly Asp Glu
        35                  40                  45

Asp Asp Lys Asn Ile Gly Ser Asp Glu Asp His Leu Ser Leu Lys Glu
    50                  55                  60

Phe Ser Glu Leu Glu Gln Ser Gly Tyr Tyr Val Cys Tyr Pro Arg Gly
65                  70                  75                  80

Ser Lys Pro Glu Asp Ala Asn Phe Tyr Leu Tyr Leu Arg Ala Arg Val
                85                  90                  95

Cys Glu Asn Cys Met Glu Met Asp
                100
```

<210> SEQ ID NO 39
<211> LENGTH: 207
<212> TYPE: PRT
<213> ORGANISM: Artificial Sequence
<220> FEATURE:
<223> OTHER INFORMATION: Human CD3 epsilon

<400> SEQUENCE: 39

```
Met Gln Ser Gly Thr His Trp Arg Val Leu Gly Leu Cys Leu Leu Ser
1               5                   10                  15

Val Gly Val Trp Gly Gln Asp Gly Asn Glu Glu Met Gly Gly Ile Thr
            20                  25                  30

Gln Thr Pro Tyr Lys Val Ser Ile Ser Gly Thr Thr Val Ile Leu Thr
        35                  40                  45

Cys Pro Gln Tyr Pro Gly Ser Glu Ile Leu Trp Gln His Asn Asp Lys
    50                  55                  60

Asn Ile Gly Gly Asp Glu Asp Asp Lys Asn Ile Gly Ser Asp Glu Asp
65                  70                  75                  80

His Leu Ser Leu Lys Glu Phe Ser Glu Leu Glu Gln Ser Gly Tyr Tyr
                85                  90                  95

Val Cys Tyr Pro Arg Gly Ser Lys Pro Glu Asp Ala Asn Phe Tyr Leu
            100                 105                 110

Tyr Leu Arg Ala Arg Val Cys Glu Asn Cys Met Glu Met Asp Val Met
        115                 120                 125

Ser Val Ala Thr Ile Val Ile Val Asp Ile Cys Ile Thr Gly Gly Leu
    130                 135                 140

Leu Leu Leu Val Tyr Tyr Trp Ser Lys Asn Arg Lys Ala Lys Ala Lys
145                 150                 155                 160

Pro Val Thr Arg Gly Ala Gly Ala Gly Gly Arg Gln Arg Gly Gln Asn
                165                 170                 175

Lys Glu Arg Pro Pro Pro Val Pro Asn Pro Asp Tyr Glu Pro Ile Arg
            180                 185                 190

Lys Gly Gln Arg Asp Leu Tyr Ser Gly Leu Asn Gln Arg Arg Ile
        195                 200                 205
```

<210> SEQ ID NO 40
<211> LENGTH: 721
<212> TYPE: PRT
<213> ORGANISM: Artificial Sequence
<220> FEATURE:
<223> OTHER INFORMATION: anti-CD3 antibody(Hu38E4.v1)

<400> SEQUENCE: 40

```
Met Asp Ser Gln Ala Gln Val Leu Met Leu Leu Leu Leu Trp Val Ser
1               5                   10                  15

Gly Thr Cys Gly Asp Ile Val Met Thr Gln Ser Pro Asp Ser Leu Ala
            20                  25                  30

Val Ser Leu Gly Glu Arg Ala Thr Ile Asn Cys Lys Ser Ser Gln Ser
        35                  40                  45

Leu Leu Asn Ser Arg Thr Arg Lys Asn Tyr Leu Ala Trp Tyr Gln Gln
    50                  55                  60

Lys Pro Gly Gln Ser Pro Lys Leu Leu Ile Tyr Trp Thr Ser Thr Arg
65                  70                  75                  80

Lys Ser Gly Val Pro Asp Arg Phe Ser Gly Ser Gly Ser Gly Thr Asp
                85                  90                  95

Phe Thr Leu Thr Ile Ser Ser Leu Gln Ala Glu Asp Val Ala Val Tyr
```

```
            100                 105                 110
Tyr Cys Lys Gln Ser Phe Ile Leu Arg Thr Phe Gly Gln Gly Thr Lys
            115                 120                 125
Val Glu Ile Lys Arg Thr Val Ala Ala Pro Ser Val Phe Ile Phe Pro
            130                 135                 140
Pro Ser Asp Glu Gln Leu Lys Ser Gly Thr Ala Ser Val Val Cys Leu
145                 150                 155                 160
Leu Asn Asn Phe Tyr Pro Arg Glu Ala Lys Val Gln Trp Lys Val Asp
            165                 170                 175
Asn Ala Leu Gln Ser Gly Asn Ser Gln Glu Ser Val Thr Glu Gln Asp
            180                 185                 190
Ser Lys Asp Ser Thr Tyr Ser Leu Ser Ser Thr Leu Thr Leu Ser Lys
            195                 200                 205
Ala Asp Tyr Glu Lys His Lys Val Tyr Ala Cys Glu Val Thr His Gln
            210                 215                 220
Gly Leu Ser Ser Pro Val Thr Lys Ser Phe Asn Arg Gly Glu Cys Ser
225                 230                 235                 240
Gly Gly Gly Ser Gly Gly Gly Ser Glu Gly Gly Ser Glu Gly Gly
            245                 250                 255
Gly Ser Glu Gly Gly Ser Glu Gly Gly Ser Gly Gly Gly Ser
            260                 265                 270
Gly Glu Val Gln Leu Val Gln Ser Gly Ala Glu Val Lys Lys Pro Gly
            275                 280                 285
Ala Ser Val Lys Val Ser Cys Lys Ala Ser Gly Phe Thr Phe Thr Ser
290                 295                 300
Tyr Tyr Ile His Trp Val Arg Gln Ala Pro Gly Gln Gly Leu Glu Trp
305                 310                 315                 320
Ile Gly Trp Ile Tyr Pro Glu Asn Asp Asn Thr Lys Tyr Asn Glu Lys
            325                 330                 335
Phe Lys Asp Arg Val Thr Ile Thr Ala Asp Thr Ser Thr Ser Thr Ala
            340                 345                 350
Tyr Leu Glu Leu Ser Ser Leu Arg Ser Glu Asp Thr Ala Val Tyr Tyr
            355                 360                 365
Cys Ala Arg Asp Gly Tyr Ser Arg Tyr Tyr Phe Asp Tyr Trp Gly Gln
            370                 375                 380
Gly Thr Leu Val Thr Val Ser Ser Ala Ser Thr Lys Gly Pro Ser Val
385                 390                 395                 400
Phe Pro Leu Ala Pro Ser Ser Lys Ser Thr Ser Gly Gly Thr Ala Ala
            405                 410                 415
Leu Gly Cys Leu Val Lys Asp Tyr Phe Pro Glu Pro Val Thr Val Ser
            420                 425                 430
Trp Asn Ser Gly Ala Leu Thr Ser Gly Val His Thr Phe Pro Ala Val
            435                 440                 445
Leu Gln Ser Ser Gly Leu Tyr Ser Leu Ser Ser Val Val Thr Val Pro
            450                 455                 460
Ser Ser Ser Leu Gly Thr Gln Thr Tyr Ile Cys Asn Val Asn His Lys
465                 470                 475                 480
Pro Ser Asn Thr Lys Val Asp Lys Lys Val Glu Pro Lys Ser Cys Asp
            485                 490                 495
Lys Thr His Thr Cys Pro Pro Cys Pro Ala Pro Glu Ala Ala Gly Gly
            500                 505                 510
Pro Ser Val Phe Leu Phe Pro Pro Lys Pro Lys Asp Thr Leu Met Ile
            515                 520                 525
```

```
Ser Arg Thr Pro Glu Val Thr Cys Val Val Val Asp Val Ser His Glu
    530                 535                 540
Asp Pro Glu Val Lys Phe Asn Trp Tyr Val Asp Gly Val Glu Val His
545                 550                 555                 560
Asn Ala Lys Thr Lys Pro Arg Glu Glu Gln Tyr Asn Ser Thr Tyr Arg
                565                 570                 575
Val Val Ser Val Leu Thr Val Leu His Gln Asp Trp Leu Asn Gly Lys
            580                 585                 590
Glu Tyr Lys Cys Lys Val Ser Asn Lys Ala Leu Pro Ala Pro Ile Glu
        595                 600                 605
Lys Thr Ile Ser Lys Ala Lys Gly Gln Pro Arg Glu Pro Arg Val Tyr
    610                 615                 620
Thr Leu Pro Pro Cys Arg Asp Glu Leu Thr Lys Asn Gln Val Ser Leu
625                 630                 635                 640
Thr Cys Leu Val Lys Gly Phe Tyr Pro Ser Asp Ile Ala Val Glu Trp
                645                 650                 655
Glu Ser Asn Gly Gln Pro Glu Asn Asn Tyr Lys Thr Thr Pro Pro Val
            660                 665                 670
Leu Val Ser Asp Gly Ser Phe Thr Leu Tyr Ser Lys Leu Thr Val Asp
        675                 680                 685
Lys Ser Arg Trp Gln Gln Gly Asn Val Phe Ser Cys Ser Val Met His
    690                 695                 700
Glu Ala Leu His Asn His Tyr Thr Gln Lys Ser Leu Ser Leu Ser Pro
705                 710                 715                 720
Gly

<210> SEQ ID NO 41
<211> LENGTH: 722
<212> TYPE: PRT
<213> ORGANISM: Artificial Sequence
<220> FEATURE:
<223> OTHER INFORMATION: anti-CD3 antibody(E15)

<400> SEQUENCE: 41

Met Asp Ser Gln Ala Gln Val Leu Met Leu Leu Leu Trp Val Ser
1               5                   10                  15
Gly Thr Cys Gly Gln Ala Val Val Thr Gln Glu Pro Ser Leu Thr Val
            20                  25                  30
Ser Pro Gly Gly Thr Val Thr Leu Thr Cys Arg Ser Ser Thr Gly Ala
        35                  40                  45
Val Thr Thr Ser Asn Tyr Ala Asn Trp Val Gln Gln Lys Pro Gly Gln
    50                  55                  60
Ala Pro Arg Gly Leu Ile Gly Gly Thr Asn Lys Arg Ala Pro Trp Thr
65                  70                  75                  80
Pro Ala Arg Phe Ser Gly Ser Leu Leu Gly Gly Lys Ala Ala Leu Thr
                85                  90                  95
Leu Ser Gly Ala Gln Pro Glu Asp Glu Ala Glu Tyr Tyr Cys Ala Leu
            100                 105                 110
Trp Tyr Ser Asn Leu Trp Val Phe Gly Gly Gly Thr Lys Leu Thr Val
        115                 120                 125
Leu Gly Gln Pro Lys Ala Asn Pro Thr Val Thr Leu Phe Pro Pro Ser
    130                 135                 140
Ser Glu Glu Leu Gln Ala Asn Lys Ala Thr Leu Val Cys Leu Ile Ser
145                 150                 155                 160
```

```
Asp Phe Tyr Pro Gly Ala Val Thr Val Ala Trp Lys Ala Asp Gly Ser
                165                 170                 175

Pro Val Lys Ala Gly Val Glu Thr Thr Lys Pro Ser Lys Gln Ser Asn
            180                 185                 190

Asn Lys Tyr Ala Ala Ser Ser Tyr Leu Ser Leu Thr Pro Glu Gln Trp
        195                 200                 205

Lys Ser His Arg Ser Tyr Ser Cys Gln Val Thr His Glu Gly Ser Thr
    210                 215                 220

Val Glu Lys Thr Val Ala Pro Thr Glu Cys Ser Gly Gly Gly Ser Gly
225                 230                 235                 240

Gly Gly Ser Glu Gly Gly Ser Glu Gly Gly Ser Glu Gly Ser Glu Gly
                245                 250                 255

Gly Ser Glu Gly Gly Ser Gly Gly Gly Ser Gly Glu Val Gln Leu
                260                 265                 270

Val Glu Ser Gly Gly Gly Leu Val Gln Pro Gly Gly Ser Leu Lys Leu
            275                 280                 285

Ser Cys Ala Ala Ser Gly Phe Thr Phe Asn Thr Tyr Ala Met Asn Trp
        290                 295                 300

Val Arg Gln Ala Ser Gly Lys Gly Leu Glu Trp Val Ala Arg Ile Arg
305                 310                 315                 320

Ser Lys Tyr Asn Asn Tyr Ala Thr Tyr Tyr Ala Asp Ser Val Lys Asp
                325                 330                 335

Arg Phe Thr Ile Ser Arg Asp Asp Ser Lys Asn Thr Ala Tyr Leu Gln
            340                 345                 350

Met Asn Ser Leu Lys Thr Glu Asp Thr Ala Val Tyr Tyr Cys Val Arg
        355                 360                 365

His Gly Asn Phe Gly Asn Ser Tyr Val Ser Trp Phe Ala Tyr Trp Gly
    370                 375                 380

Gln Gly Thr Leu Val Thr Val Ser Ser Ala Ser Thr Lys Gly Pro Ser
385                 390                 395                 400

Val Phe Pro Leu Ala Pro Ser Ser Lys Ser Thr Ser Gly Gly Thr Ala
                405                 410                 415

Ala Leu Gly Cys Leu Val Lys Asp Tyr Phe Pro Glu Pro Val Thr Val
            420                 425                 430

Ser Trp Asn Ser Gly Ala Leu Thr Ser Gly Val His Thr Phe Pro Ala
        435                 440                 445

Val Leu Gln Ser Ser Gly Leu Tyr Ser Leu Ser Ser Val Val Thr Val
    450                 455                 460

Pro Ser Ser Ser Leu Gly Thr Gln Thr Tyr Ile Cys Asn Val Asn His
465                 470                 475                 480

Lys Pro Ser Asn Thr Lys Val Asp Lys Lys Val Glu Pro Lys Ser Cys
                485                 490                 495

Asp Lys Thr His Thr Cys Pro Pro Cys Pro Ala Pro Glu Ala Ala Gly
            500                 505                 510

Gly Pro Ser Val Phe Leu Phe Pro Pro Lys Pro Lys Asp Thr Leu Met
        515                 520                 525

Ile Ser Arg Thr Pro Glu Val Thr Cys Val Val Val Asp Val Ser His
    530                 535                 540

Glu Asp Pro Glu Val Lys Phe Asn Trp Tyr Val Asp Gly Val Glu Val
545                 550                 555                 560

His Asn Ala Lys Thr Lys Pro Arg Glu Glu Gln Tyr Asn Ser Thr Tyr
                565                 570                 575

Arg Val Val Ser Val Leu Thr Val Leu His Gln Asp Trp Leu Asn Gly
```

```
                       580                 585                 590
Lys Glu Tyr Lys Cys Lys Val Ser Asn Lys Ala Leu Pro Ala Pro Ile
                595                 600                 605

Glu Lys Thr Ile Ser Lys Ala Lys Gly Gln Pro Arg Glu Pro Arg Val
            610                 615                 620

Tyr Thr Leu Pro Pro Cys Arg Asp Glu Leu Thr Lys Asn Gln Val Ser
625                 630                 635                 640

Leu Thr Cys Leu Val Lys Gly Phe Tyr Pro Ser Asp Ile Ala Val Glu
                645                 650                 655

Trp Glu Ser Asn Gly Gln Pro Glu Asn Asn Tyr Lys Thr Thr Pro Pro
            660                 665                 670

Val Leu Val Ser Asp Gly Ser Phe Thr Leu Tyr Ser Lys Leu Thr Val
                675                 680                 685

Asp Lys Ser Arg Trp Gln Gln Gly Asn Val Phe Ser Cys Ser Val Met
            690                 695                 700

His Glu Ala Leu His Asn His Tyr Thr Gln Lys Ser Leu Ser Leu Ser
705                 710                 715                 720

Pro Gly

<210> SEQ ID NO 42
<211> LENGTH: 113
<212> TYPE: PRT
<213> ORGANISM: Artificial Sequence
<220> FEATURE:
<223> OTHER INFORMATION: Variable Light chain of anti-CD3
      antibody(Hu38E4.v1)

<400> SEQUENCE: 42

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Arg Thr Arg Lys Asn Tyr Leu Ala Trp Tyr Gln Gln Lys Pro Gly Gln
        35                  40                  45

Ser Pro Lys Leu Leu Ile Tyr Trp Thr Ser Thr Arg Lys Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Lys Gln
                85                  90                  95

Ser Phe Ile Leu Arg Thr Phe Gly Gln Gly Thr Lys Val Glu Ile Lys
            100                 105                 110

Arg

<210> SEQ ID NO 43
<211> LENGTH: 110
<212> TYPE: PRT
<213> ORGANISM: Artificial Sequence
<220> FEATURE:
<223> OTHER INFORMATION: Variable Light chain of anti-CD3 antibody(A15,
      E15)

<400> SEQUENCE: 43

Gln Ala Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30
```

Asn Tyr Ala Asn Trp Val Gln Gln Lys Pro Gly Gln Ala Pro Arg Gly
                35                  40                  45

Leu Ile Gly Gly Thr Asn Lys Arg Ala Pro Trp Thr Pro Ala Arg Phe
 50                  55                  60

Ser Gly Ser Leu Leu Gly Gly Lys Ala Ala Leu Thr Leu Ser Gly Ala
 65                  70                  75                  80

Gln Pro Glu Asp Glu Ala Glu Tyr Tyr Cys Ala Leu Trp Tyr Ser Asn
                 85                  90                  95

Leu Trp Val Phe Gly Gly Gly Thr Lys Leu Thr Val Leu Gly
                100                 105                 110

<210> SEQ ID NO 44
<211> LENGTH: 119
<212> TYPE: PRT
<213> ORGANISM: Artificial Sequence
<220> FEATURE:
<223> OTHER INFORMATION: Variable heavy chain of anti-CD3
      antibody(Hu38E4.v1)

<400> SEQUENCE: 44

Glu Val Gln Leu Val Gln Ser Gly Ala Glu Val Lys Lys Pro Gly Ala
 1               5                  10                  15

Ser Val Lys Val Ser Cys Lys Ala Ser Gly Phe Thr Phe Thr Ser Tyr
                20                  25                  30

Tyr Ile His Trp Val Arg Gln Ala Pro Gly Gln Gly Leu Glu Trp Ile
                35                  40                  45

Gly Trp Ile Tyr Pro Glu Asn Asp Asn Thr Lys Tyr Asn Glu Lys Phe
 50                  55                  60

Lys Asp Arg Val Thr Ile Thr Ala Asp Thr Ser Thr Ser Thr Ala Tyr
 65                  70                  75                  80

Leu Glu Leu Ser Ser Leu Arg Ser Glu Asp Thr Ala Val Tyr Tyr Cys
                 85                  90                  95

Ala Arg Asp Gly Tyr Ser Arg Tyr Tyr Phe Asp Tyr Trp Gly Gln Gly
                100                 105                 110

Thr Leu Val Thr Val Ser Ser
        115

<210> SEQ ID NO 45
<211> LENGTH: 125
<212> TYPE: PRT
<213> ORGANISM: Artificial Sequence
<220> FEATURE:
<223> OTHER INFORMATION: Variable heavy chain of anti-CD3 antibody(A15)

<400> SEQUENCE: 45

Glu Val Gln Leu Val Glu Ser Gly Gly Gly Leu Val Gln Pro Gly Gly
 1               5                  10                  15

Ser Leu Lys Leu Ser Cys Ala Ala Ser Gly Phe Thr Phe Asn Thr Tyr
                20                  25                  30

Ala Met Asn Trp Val Arg Gln Ala Ser Gly Lys Gly Leu Glu Trp Val
                35                  40                  45

Gly Arg Ile Arg Ser Lys Tyr Asn Asn Tyr Ala Thr Tyr Tyr Ala Asp
 50                  55                  60

Ser Val Lys Asp Arg Phe Thr Ile Ser Arg Asp Asp Ser Lys Asn Thr
 65                  70                  75                  80

Ala Tyr Leu Gln Met Asn Ser Leu Lys Thr Glu Asp Thr Ala Val Tyr
                 85                  90                  95

Tyr Cys Val Arg His Gly Asn Phe Gly Asn Ser Tyr Val Ser Trp Phe

```
            100                 105                 110
Ala Tyr Trp Gly Gln Gly Thr Leu Val Thr Val Ser Ser
        115                 120                 125

<210> SEQ ID NO 46
<211> LENGTH: 125
<212> TYPE: PRT
<213> ORGANISM: Artificial Sequence
<220> FEATURE:
<223> OTHER INFORMATION: Variable heavy chain of anti-CD3 antibody(E15)

<400> SEQUENCE: 46

Glu Val Gln Leu Val Glu Ser Gly Gly Leu Val Gln Pro Gly Gly
1               5                   10                  15

Ser Leu Lys Leu Ser Cys Ala Ala Ser Gly Phe Thr Phe Asn Thr Tyr
                20                  25                  30

Ala Met Asn Trp Val Arg Gln Ala Ser Gly Lys Gly Leu Glu Trp Val
            35                  40                  45

Ala Arg Ile Arg Ser Lys Tyr Asn Asn Tyr Ala Thr Tyr Tyr Ala Asp
        50                  55                  60

Ser Val Lys Asp Arg Phe Thr Ile Ser Arg Asp Asp Ser Lys Asn Thr
65                  70                  75                  80

Ala Tyr Leu Gln Met Asn Ser Leu Lys Thr Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125

<210> SEQ ID NO 47
<211> LENGTH: 329
<212> TYPE: PRT
<213> ORGANISM: Artificial Sequence
<220> FEATURE:
<223> OTHER INFORMATION: Fc region with Hole structure

<400> SEQUENCE: 47

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Ala Ala Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160
```

-continued

```
Tyr Val Asp Gly Val Glu Val His Asn Ala Lys Thr Lys Pro Arg Glu
                165                 170                 175
Glu Gln Tyr Asn Ser Thr Tyr Arg Val Val Ser Val Leu Thr Val Leu
            180                 185                 190
His Gln Asp Trp Leu Asn Gly Lys Glu Tyr Lys Cys Lys Val Ser Asn
        195                 200                 205
Lys Ala Leu Pro Ala Pro Ile Glu Lys Thr Ile Ser Lys Ala Lys Gly
    210                 215                 220
Gln Pro Arg Glu Pro Arg Val Tyr Thr Leu Pro Pro Cys Arg Asp Glu
225                 230                 235                 240
Leu Thr Lys Asn Gln Val Ser Leu Thr Cys Leu Val Lys Gly Phe Tyr
                245                 250                 255
Pro Ser Asp Ile Ala Val Glu Trp Glu Ser Asn Gly Gln Pro Glu Asn
            260                 265                 270
Asn Tyr Lys Thr Thr Pro Pro Val Leu Val Ser Asp Gly Ser Phe Thr
        275                 280                 285
Leu Tyr Ser Lys Leu Thr Val Asp Lys Ser Arg Trp Gln Gln Gly Asn
    290                 295                 300
Val Phe Ser Cys Ser Val Met His Glu Ala Leu His Asn His Tyr Thr
305                 310                 315                 320
Gln Lys Ser Leu Ser Leu Ser Pro Gly
                325

<210> SEQ ID NO 48
<211> LENGTH: 329
<212> TYPE: PRT
<213> ORGANISM: Artificial Sequence
<220> FEATURE:
<223> OTHER INFORMATION: Fc region with knob structure

<400> SEQUENCE: 48

Ala Ser Thr Lys Gly Pro Ser Val Phe Pro Leu Ala Pro Ser Ser Lys
1               5                   10                  15
Ser Thr Ser Gly Gly Thr Ala Ala Leu Gly Cys Leu Val Lys Asp Tyr
            20                  25                  30
Phe Pro Glu Pro Val Thr Val Ser Trp Asn Ser Gly Ala Leu Thr Ser
        35                  40                  45
Gly Val His Thr Phe Pro Ala Val Leu Gln Ser Ser Gly Leu Tyr Ser
    50                  55                  60
Leu Ser Ser Val Val Thr Val Pro Ser Ser Leu Gly Thr Gln Thr
65                  70                  75                  80
Tyr Ile Cys Asn Val Asn His Lys Pro Ser Asn Thr Lys Val Asp Lys
                85                  90                  95
Lys Val Glu Pro Lys Ser Cys Asp Lys Thr His Thr Cys Pro Pro Cys
            100                 105                 110
Pro Ala Pro Glu Ala Ala Gly Gly Pro Ser Val Phe Leu Phe Pro Pro
        115                 120                 125
Lys Pro Lys Asp Thr Leu Met Ile Ser Arg Thr Pro Glu Val Thr Cys
    130                 135                 140
Val Val Val Asp Val Ser His Glu Asp Pro Glu Val Lys Phe Asn Trp
145                 150                 155                 160
Tyr Val Asp Gly Val Glu Val His Asn Ala Lys Thr Lys Pro Arg Glu
                165                 170                 175
Glu Gln Tyr Asn Ser Thr Tyr Arg Val Val Ser Val Leu Thr Val Leu
            180                 185                 190
```

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
    210                 215                 220

Gln Pro Arg Glu Pro Gln Val Cys Thr Leu Pro Pro Ser Arg Asp Glu
225                 230                 235                 240

Leu Thr Glu Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Trp Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly
            325

<210> SEQ ID NO 49
<211> LENGTH: 250
<212> TYPE: PRT
<213> ORGANISM: Artificial Sequence
<220> FEATURE:
<223> OTHER INFORMATION: scFv of A15

<400> SEQUENCE: 49

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Asn Thr Tyr
            20                  25                  30

Ala Met Asn Trp Val Arg Gln Ala Ser Gly Lys Cys Leu Glu Trp Val
        35                  40                  45

Gly Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Asn Thr
65                  70                  75                  80

Ala Tyr Leu Gln Met Asn Ser Leu Lys Thr Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser Gly Gly Gly
        115                 120                 125

Gly Ser Gly Gly Gly Gly Ser Gly Gly Gly Gly Ser Gln Ala Val Val
    130                 135                 140

Thr Gln Glu Pro Ser Leu Thr Val Ser Pro Gly Gly Thr Val Thr Leu
145                 150                 155                 160

Thr Cys Arg Ser Ser Thr Gly Ala Val Thr Thr Ser Asn Tyr Ala Asn
                165                 170                 175

Trp Val Gln Gln Lys Pro Gly Gln Ala Pro Arg Gly Leu Ile Gly Gly
            180                 185                 190

Thr Asn Lys Arg Ala Pro Trp Thr Pro Ala Arg Phe Ser Gly Ser Leu
        195                 200                 205

Leu Gly Gly Lys Ala Ala Leu Thr Leu Ser Gly Ala Gln Pro Glu Asp
    210                 215                 220

```
Glu Ala Glu Tyr Tyr Cys Ala Leu Trp Tyr Ser Asn Leu Trp Val Phe
225                 230                 235                 240

Gly Cys Gly Thr Lys Leu Thr Val Leu Gly
                245                 250
```

<210> SEQ ID NO 50
<211> LENGTH: 750
<212> TYPE: DNA
<213> ORGANISM: Artificial Sequence
<220> FEATURE:
<223> OTHER INFORMATION: scFv of A15

<400> SEQUENCE: 50

```
gaagtacaac tggtggagtc agggggaggt cttgtccagc cgggagggtc tttgaaattg      60
agctgcgcag ccagcgggtt cacttttaac acttacgcaa tgaactgggt gcggcaggcc     120
agcggcaaat gcttggagtg ggtaggcaga atccgatcaa aatacaataa ctacgcgact     180
tattacgcgg actccgtcaa agatcggttc actatatctc gggatgatag caagaacact     240
gcgtacctcc aaatgaattc acttaagact gaggatactg cagtctatta ctgtgtcagg     300
cacggcaact tcggaaactc ttacgtgagc tggttcgcgt actgggggca aggcaccctc     360
gttaccgtga gtagtggcgg aggtggctct ggggggggtg gctccggtgg tggaggaagc     420
caggctgttg tcacgcaaga acctagtttg accgtctctc cggtggaac ggttaccctc     480 acttgtagat cttctaccgg agcggtaact acttctaatt acgcgaactg gtacaacaa     540 aaaccgggtc aagctccccg aggtctcata ggcggaacca acaagcgagc tccctggact     600
ccagcacggt tcagtggtag tttgcttggg ggtaaagcag cccttacgct ttcaggcgct     660
cagcctgaag acgaagctga gtattattgc gcgctctggt actccaatct ctgggttttt     720
ggatgcggca ctaaactgac ggtgctcggg                                     750
```

<210> SEQ ID NO 51
<211> LENGTH: 250
<212> TYPE: PRT
<213> ORGANISM: Artificial Sequence
<220> FEATURE:
<223> OTHER INFORMATION: scFv of E15

<400> SEQUENCE: 51

```
Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Asn Thr Tyr
            20                  25                  30

Ala Met Asn Trp Val Arg Gln Ala Ser Gly Lys Cys Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Asn Thr
65                  70                  75                  80

Ala Tyr Leu Gln Met Asn Ser Leu Lys Thr Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser Gly Gly Gly
        115                 120                 125

Gly Ser Gly Gly Gly Gly Ser Gly Gly Gly Gly Ser Gln Ala Val Val
    130                 135                 140
```

```
Thr Gln Glu Pro Ser Leu Thr Val Ser Pro Gly Gly Thr Val Thr Leu
145                 150                 155                 160

Thr Cys Arg Ser Ser Thr Gly Ala Val Thr Thr Ser Asn Tyr Ala Asn
                165                 170                 175

Trp Val Gln Gln Lys Pro Gly Gln Ala Pro Arg Gly Leu Ile Gly Gly
            180                 185                 190

Thr Asn Lys Arg Ala Pro Trp Thr Pro Ala Arg Phe Ser Gly Ser Leu
        195                 200                 205

Leu Gly Gly Lys Ala Ala Leu Thr Leu Ser Gly Ala Gln Pro Glu Asp
    210                 215                 220

Glu Ala Glu Tyr Tyr Cys Ala Leu Trp Tyr Ser Asn Leu Trp Val Phe
225                 230                 235                 240

Gly Cys Gly Thr Lys Leu Thr Val Leu Gly
                245                 250

<210> SEQ ID NO 52
<211> LENGTH: 750
<212> TYPE: DNA
<213> ORGANISM: Artificial Sequence
<220> FEATURE:
<223> OTHER INFORMATION: scFv of E15

<400> SEQUENCE: 52
gaggtgcaac tggtcgagtc tggaggagga ctcgtgcaac caggggggag cttgaagctg      60
tcttgtgctg cgagtgggtt tacgttcaat acttatgcca tgaactgggt caggcaggct     120
tccgggaagt gtttggagtg ggtggcacgc atccgaagca aatataacaa ttatgctact     180
tactacgctg attcagtcaa ggatcgcttc accataagcc gcgatgattc aaaaaacact     240
gcatatctcc agatgaatag tctgaagact gaagatacgg cggtgtatta ctgtgtaagg     300
cacgggaact ttgggaacag ttacgtgagt tggtttgcat attggggtca gggtacgctg     360
gttaccgtga gcagcggggg tggagggagc ggggcggcg ttctggcgg cggtgggtct       420 caagctgtgg ttacccagga gccctcactc actgtctcac caggtggcac agtcacactt     480
acatgtcgaa gtagcacagg ggcggtcacg acttccaact acgctaactg ggttcaacaa     540
aaaccggggc aggcacctcg gggactgatt ggggtacaa ataagagggc accctggact      600
ccagcccgct tttcaggcag cctgctcggg gtaaagctg cactcactct ttctggagcg     660
caacctgaag atgaggcaga atactactgc gcactttggt actccaacct gtgggttttc     720
ggatgcggta ctaagctgac agtactcggg                                     750

<210> SEQ ID NO 53
<211> LENGTH: 2142
<212> TYPE: DNA
<213> ORGANISM: Artificial Sequence
<220> FEATURE:
<223> OTHER INFORMATION: anti-GPNMB1-VL-CL-linker-VH-CH (Knob vector)

<400> SEQUENCE: 53
atggatagtc aagcccaggt gctgatgctt ctgctgctgt gggtaagcgg tacctgtggc      60
cagtctgtgc tgactcagcc accctcagcg tctgggaccc ccgggcagag ggtcaccatc     120
tcttgtagtg gctcttcatc taatattggc aataattatg tctcctggta ccagcagctc     180
ccaggaacgg cccccaaact cctcatctat gctgatagtc agcggccaag cggggtccct     240
gaccgattct ctggctccaa gtctggcacc tcagcctccc tggccatcag tgggctccgg     300
tccgaggatg aggctgatta ttactgtggt gcttgggatt ctagcctgaa tgcttatgtc     360
```

```
ttcggcggag gcaccaagct gacggtccta ggccagccaa aggccaaccc aactgtgaca        420
ctgtttcccc ccagctcaga agagctgcag gctaataaag cgaccctggt ttgtctgata        480
agtgacttct accctggcgc cgttaccgtg gcttggaagg ccgatggctc gccagtgaag        540
gccggcgtgg agaccacaaa accaagcaag cagagcaata acaaatacgc tgcaagcagc        600
tatctgagct tgacccctga gcagtggaaa agccacagaa gctatagttg ccaggtgaca        660
cacgaaggaa gcactgtaga aaagaccgtt gcacccactg aatgtagcgg gggtgggtct        720
ggcggtggct ctgagggcgg aggcagcgag ggggtggct ctgagggcgg cgggtctgaa         780
ggaggcggct caggtggggg ctcaggcgag gtgcagctgt tggagtctgg gggaggcttg        840
gtacagcctg gggggtccct gagactctcc tgtgcagcct ctggattcac ctttagcaat        900
tatgctatga gctgggtccg ccaggctcca gggaaggggc tggagtgggt ctcatcgatc        960
tctcatagtg gtggtagtaa atattacgct gattctgtaa aaggtcggtt caccatctcc       1020
agagacaatt ccaagaacac gctgtatctg caaatgaaca gcctgagagc cgaggacacg       1080
gccgtgtatt actgtgcgag aaagtggtcg actttcgact actggggcca gggtacactg       1140
gtcaccgtga gctcagcctc caccaagggc ccaagtgtgt tcccacttgc ccccagcagc       1200
aagtctacaa gcggcgggac agctgctcta ggttgcctgg ttaaggacta tttccctgag       1260
ccagttacag taagttggaa tagcggcgcc cttacaagtg gggtccatac ttttccagca       1320
gtactgcagt cgtcgggtct ctatagtctg agctctgtgg taacggtgcc atctagctca       1380
cttggcactc agacctacat ctgcaacgtg aaccataaac ccagcaacac caaagtcgac       1440
aagaaagttg aacccaagtc ctgcgataaa actcacacgt gtcctccatg tcctgctccc       1500
gaggccgcag gcggacccag tgtgtttctg tttcctccga aacctaagga taccctaatg       1560
atttcacgga ccccagaggt gacgtgcgtg gtggtggatg tgtcacatga ggaccccgag       1620
gtcaaattca attggtacgt ggacggcgtg gaagttcaca cgctaaaaac caaacccagg       1680
gaagaacagt acaatagcac atatagagtt gtgtcagtcc tgacagtgct gcaccaggat       1740
tggctgaatg gcaaggagta caagtgcaag gtgagcaaca aggccttgcc tgcaccaatc       1800
gagaaaacca tttctaaggc caagggccaa ccccgcgaac cccaagtgtg taccctgccc       1860
ccctctagag acgagctcac tgaaaaccag gtgagcttaa cttgtctggt aagggattc        1920
tacccaagcg acatagccgt agaatgggag agcaatggtc aacccgaaaa taactataaa       1980
acaactcctc ctgtgctgga tagcgacggc agttttttcc tgtatagctg gctgaccgtg       2040
gataagtcta gatggcagca ggggaatgtc tttagctgtt ctgtgatgca cgaggcgctc       2100
cataaccact acacccagaa gagcttgagc ttgagcccag ga                         2142
```

<210> SEQ ID NO 54
<211> LENGTH: 2142
<212> TYPE: DNA
<213> ORGANISM: Artificial Sequence
<220> FEATURE:
<223> OTHER INFORMATION: anti-GPNMB6-VL-CL-linker-VH-CH (Knob vector)

<400> SEQUENCE: 54

```
atggatagtc aagcccaggt gctgatgctt ctgctgctgt gggtaagcgg tacctgtggc         60
cagtctgtgc tgactcagcc accctcagcg tctgggaccc ccgggcagag ggtcaccatc        120
tcttgtagtg gctcttcatc taatattggc aataattatg tctcctggta ccagcagctc        180
ccaggaacgg cccccaaact cctcatctat gctgatagtc agcggccaag cggggtccct        240
gaccgattct ctggctccaa gtctggcacc tcagcctccc tggccatcag tgggctccgg        300
```

```
tccgaggatg aggctgatta ttactgtggt gcttgggatt ctagcctgaa tgcttatgtc      360
ttcggcggag gcaccaagct gacggtccta ggccagccaa aggccaaccc aactgtgaca      420
ctgtttcccc ccagctcaga agagctgcag gctaataaag cgaccctggt ttgtctgata      480
agtgacttct accctggcgc cgttaccgtg gcttggaagg ccgatggctc gccagtgaag      540
gccggcgtgg agaccacaaa accaagcaag cagagcaata acaaatacgc tgcaagcagc      600
tatctgagct tgaccectga gcagtggaaa agccacagaa gctatagttg ccaggtgaca      660
cacgaaggaa gcactgtaga aaagaccgtt gcacccactg aatgtagcgg gggtgggtct      720
ggcggtggct ctgagggcgg aggcagcgag gggggtggct ctgagggcgg cgggtctgaa      780
ggaggcggct caggtggggg ctcaggcgag gtgcagctgt ggagtctggg ggaggcttg      840 gtacagcctg gggggtccct gagactctcc tgtgcagcct ctggattcac ctttgcagcc      900
cgaccaatga gctgggtccg ccaggctcca gggaaggggc tggagtgggt ctcatcgatc      960
tctcatagtg gtggtagtaa atattacgct gattctgtaa aaggtcggtt caccatctcc     1020
agagacaatt ccaagaacac gctgtatctg caaatgaaca gcctgagagc cgaggacacg     1080
gccgtgtatt actgtgcgag aaagtggtcg actttcgact actggggcca gggtacactg     1140
gtcaccgtga gctcagcctc caccaagggc ccaagtgtgt tcccacttgc ccccagcagc     1200
aagtctacaa gcggcgggac agctgctcta ggttgcctgg ttaaggacta tttccctgag     1260
ccagttacag taagttggaa tagcggcgcc cttacaagtg gggtccatac ttttccagca     1320
gtactgcagt cgtcgggtct ctatagtctg agctctgtgg taacggtgcc atctagctca     1380
cttggcactc agacctacat ctgcaacgtg aaccataaac ccagcaacac caaagtcgac     1440
aagaaagttg aacccaagtc ctgcgataaa actcacacgt gtcctccatg tcctgctccc     1500
gaggccgcag gcggacccag tgtgtttctg tttcctccga aacctaagga tacectaatg     1560 atttcacgga ccccagaggt gacgtgcgtg gtggtggatg tgtcacatga ggacccggag     1620
gtcaaattca attggtacgt ggacggcgtg gaagttcaca cgctaaaac caaacccagg     1680 gaagaacagt acaatagcac atatagagtt gtgtcagtcc tgacagtgct gcaccaggat     1740
tggctgaatg gcaaggagta caagtgcaag gtgagcaaca aggccttgcc tgcaccaatc     1800
gagaaaacca tttctaaggc caagggccaa ccccgcgaac cccaagtgtg taccctgccc     1860
ccctctagag acgagctcac tgaaaaccag gtgagcttaa cttgtctggt gaagggattc     1920
tacccaagcg acatagccgt agaatgggag agcaatggtc aacccgaaaa taactataaa     1980
acaactcctc ctgtgctgga tagcgacggc agttttttcc tgtatagctg gctgaccgtg     2040
gataagtcta gatggcagca ggggaatgtc tttagctgtt ctgtgatgca cgaggcgctc     2100
cataaccact acacccagaa gagcttgagc ttgagcccag ga                      2142
```

<210> SEQ ID NO 55
<211> LENGTH: 385
<212> TYPE: PRT
<213> ORGANISM: Artificial Sequence
<220> FEATURE:
<223> OTHER INFORMATION: GPNMB1

<400> SEQUENCE: 55

Met Asp Ser Gln Ala Gln Val Leu Met Leu Leu Leu Leu Trp Val Ser
1               5                   10                  15

Gly Thr Cys Gly Gln Ser Val Leu Thr Gln Pro Pro Ser Ala Ser Gly
            20                  25                  30

```
Thr Pro Gly Gln Arg Val Thr Ile Ser Cys Ser Gly Ser Ser Ser Asn
        35                  40                  45

Ile Gly Asn Asn Tyr Val Ser Trp Tyr Gln Gln Leu Pro Gly Thr Ala
 50                  55                  60

Pro Lys Leu Leu Ile Tyr Ala Asp Ser Gln Arg Pro Ser Gly Val Pro
 65                  70                  75                  80

Asp Arg Phe Ser Gly Ser Lys Ser Gly Thr Ser Ala Ser Leu Ala Ile
                85                  90                  95

Ser Gly Leu Arg Ser Glu Asp Glu Ala Asp Tyr Tyr Cys Gly Ala Trp
            100                 105                 110

Asp Ser Ser Leu Asn Ala Tyr Val Phe Gly Gly Gly Thr Lys Leu Thr
        115                 120                 125

Val Leu Gly Gln Pro Lys Ala Asn Pro Thr Val Thr Leu Phe Pro Pro
130                 135                 140

Ser Ser Glu Glu Leu Gln Ala Asn Lys Ala Thr Leu Val Cys Leu Ile
145                 150                 155                 160

Ser Asp Phe Tyr Pro Gly Ala Val Thr Val Ala Trp Lys Ala Asp Gly
                165                 170                 175

Ser Pro Val Lys Ala Gly Val Glu Thr Thr Lys Pro Ser Lys Gln Ser
            180                 185                 190

Asn Asn Lys Tyr Ala Ala Ser Ser Tyr Leu Ser Leu Thr Pro Glu Gln
        195                 200                 205

Trp Lys Ser His Arg Ser Tyr Ser Cys Gln Val Thr His Glu Gly Ser
210                 215                 220

Thr Val Glu Lys Thr Val Ala Pro Thr Glu Cys Ser Gly Gly Gly Ser
225                 230                 235                 240

Gly Gly Gly Ser Glu Gly Gly Ser Glu Gly Gly Ser Glu Gly Glu Gly
                245                 250                 255

Gly Gly Ser Glu Gly Gly Ser Gly Gly Ser Gly Glu Val Gln
            260                 265                 270

Leu Leu Glu Ser Gly Gly Gly Leu Val Gln Pro Gly Gly Ser Leu Arg
        275                 280                 285

Leu Ser Cys Ala Ala Ser Gly Phe Thr Phe Ser Asn Tyr Ala Met Ser
290                 295                 300

Trp Val Arg Gln Ala Pro Gly Lys Gly Leu Glu Trp Val Ser Ser Ile
305                 310                 315                 320

Ser His Ser Gly Gly Ser Lys Tyr Tyr Ala Asp Ser Val Lys Gly Arg
                325                 330                 335

Phe Thr Ile Ser Arg Asp Asn Ser Lys Asn Thr Leu Tyr Leu Gln Met
            340                 345                 350

Asn Ser Leu Arg Ala Glu Asp Thr Ala Val Tyr Tyr Cys Ala Arg Lys
        355                 360                 365

Trp Ser Thr Phe Asp Tyr Trp Gly Gln Gly Thr Leu Val Thr Val Ser
370                 375                 380

Ser
385

<210> SEQ ID NO 56
<211> LENGTH: 385
<212> TYPE: PRT
<213> ORGANISM: Artificial Sequence
<220> FEATURE:
<223> OTHER INFORMATION: GPNMB2

<400> SEQUENCE: 56
```

```
Met Asp Ser Gln Ala Gln Val Leu Met Leu Leu Leu Trp Val Ser
1               5                   10                  15

Gly Thr Cys Gly Gln Ser Val Leu Thr Gln Pro Pro Ser Ala Ser
            20                  25                  30

Gly Thr Pro Gly Gln Arg Val Thr Ile Ser Cys Ser Gly Ser Ser Ser Asn
            35                  40                  45

Ile Gly Asn Asn Tyr Val Ser Trp Tyr Gln Gln Leu Pro Gly Thr Ala
50                  55                  60

Pro Lys Leu Leu Ile Tyr Ala Asp Ser Gln Arg Pro Ser Gly Val Pro
65                  70                  75                  80

Asp Arg Phe Ser Gly Ser Lys Ser Gly Thr Ser Ala Ser Leu Ala Ile
                85                  90                  95

Ser Gly Leu Arg Ser Glu Asp Glu Ala Asp Tyr Tyr Cys Gly Ala Trp
            100                 105                 110

Asp Ser Ser Leu Asn Ala Tyr Val Phe Gly Gly Gly Thr Lys Leu Thr
            115                 120                 125

Val Leu Gly Gln Pro Lys Ala Asn Pro Thr Val Thr Leu Phe Pro Pro
    130                 135                 140

Ser Ser Glu Glu Leu Gln Ala Asn Lys Ala Thr Leu Val Cys Leu Ile
145                 150                 155                 160

Ser Asp Phe Tyr Pro Gly Ala Val Thr Val Ala Trp Lys Ala Asp Gly
                165                 170                 175

Ser Pro Val Lys Ala Gly Val Glu Thr Thr Lys Pro Ser Lys Gln Ser
            180                 185                 190

Asn Asn Lys Tyr Ala Ala Ser Ser Tyr Leu Ser Leu Thr Pro Glu Gln
            195                 200                 205

Trp Lys Ser His Arg Ser Tyr Ser Cys Gln Val Thr His Glu Gly Ser
    210                 215                 220

Thr Val Glu Lys Thr Val Ala Pro Thr Glu Cys Ser Gly Gly Gly Ser
225                 230                 235                 240

Gly Gly Gly Ser Glu Gly Gly Gly Ser Glu Gly Gly Gly Ser Glu Gly
                245                 250                 255

Gly Gly Ser Glu Gly Gly Gly Ser Gly Gly Gly Ser Gly Glu Val Gln
            260                 265                 270

Leu Leu Glu Ser Gly Gly Gly Leu Val Gln Pro Gly Gly Ser Leu Arg
    275                 280                 285

Leu Ser Cys Ala Ala Ser Gly Phe Thr Phe Arg Lys Leu Asn Met Ser
    290                 295                 300

Trp Val Arg Gln Ala Pro Gly Lys Gly Leu Glu Trp Val Ser Ser Ile
305                 310                 315                 320

Ser His Ser Gly Gly Ser Lys Tyr Tyr Ala Asp Ser Val Lys Gly Arg
                325                 330                 335

Phe Thr Ile Ser Arg Asp Asn Ser Lys Asn Thr Leu Tyr Leu Gln Met
            340                 345                 350

Asn Ser Leu Arg Ala Glu Asp Thr Ala Val Tyr Tyr Cys Ala Arg Lys
    355                 360                 365

Trp Ser Thr Phe Asp Tyr Trp Gly Gln Gly Thr Leu Val Thr Val Ser
    370                 375                 380

Ser
385

<210> SEQ ID NO 57
<211> LENGTH: 385
<212> TYPE: PRT
```

<213> ORGANISM: Artificial Sequence
<220> FEATURE:
<223> OTHER INFORMATION: GPNMB3

<400> SEQUENCE: 57

```
Met Asp Ser Gln Ala Gln Val Leu Met Leu Leu Leu Trp Val Ser
1               5                   10                  15

Gly Thr Cys Gly Gln Ser Val Leu Thr Gln Pro Ser Ala Ser Gly
            20                  25                  30

Thr Pro Gly Gln Arg Val Thr Ile Ser Cys Ser Gly Ser Ser Asn
        35                  40                  45

Ile Gly Asn Asn Tyr Val Ser Trp Tyr Gln Gln Leu Pro Gly Thr Ala
50                  55                  60

Pro Lys Leu Leu Ile Tyr Ala Asp Ser Gln Arg Pro Ser Gly Val Pro
65                  70                  75                  80

Asp Arg Phe Ser Gly Ser Lys Ser Gly Thr Ser Ala Ser Leu Ala Ile
                85                  90                  95

Ser Gly Leu Arg Ser Glu Asp Glu Ala Asp Tyr Tyr Cys Gly Ala Trp
            100                 105                 110

Asp Ser Ser Leu Asn Ala Tyr Val Phe Gly Gly Gly Thr Lys Leu Thr
        115                 120                 125

Val Leu Gly Gln Pro Lys Ala Asn Pro Thr Val Thr Leu Phe Pro Pro
130                 135                 140

Ser Ser Glu Glu Leu Gln Ala Asn Lys Ala Thr Leu Val Cys Leu Ile
145                 150                 155                 160

Ser Asp Phe Tyr Pro Gly Ala Val Thr Val Ala Trp Lys Ala Asp Gly
                165                 170                 175

Ser Pro Val Lys Ala Gly Val Glu Thr Thr Lys Pro Ser Lys Gln Ser
            180                 185                 190

Asn Asn Lys Tyr Ala Ala Ser Ser Tyr Leu Ser Leu Thr Pro Glu Gln
        195                 200                 205

Trp Lys Ser His Arg Ser Tyr Ser Cys Gln Val Thr His Glu Gly Ser
210                 215                 220

Thr Val Glu Lys Thr Val Ala Pro Thr Glu Cys Ser Gly Gly Gly Ser
225                 230                 235                 240

Gly Gly Gly Ser Glu Gly Gly Ser Glu Gly Gly Ser Glu Gly
                245                 250                 255

Gly Gly Ser Glu Gly Gly Ser Gly Gly Ser Gly Glu Val Gln
            260                 265                 270

Leu Leu Glu Ser Gly Gly Leu Val Gln Pro Gly Gly Ser Leu Arg
        275                 280                 285

Leu Ser Cys Ala Ala Ser Gly Phe Thr Phe Arg Ala Arg Pro Met Ser
290                 295                 300

Trp Val Arg Gln Ala Pro Gly Lys Gly Leu Glu Trp Val Ser Ser Ile
305                 310                 315                 320

Ser His Ser Gly Gly Ser Lys Tyr Tyr Ala Asp Ser Val Lys Gly Arg
                325                 330                 335

Phe Thr Ile Ser Arg Asp Asn Ser Lys Asn Thr Leu Tyr Leu Gln Met
            340                 345                 350

Asn Ser Leu Arg Ala Glu Asp Thr Ala Val Tyr Tyr Cys Ala Arg Lys
        355                 360                 365

Trp Ser Thr Phe Asp Tyr Trp Gly Gln Gly Thr Leu Val Thr Val Ser
370                 375                 380

Ser
```

385

```
<210> SEQ ID NO 58
<211> LENGTH: 385
<212> TYPE: PRT
<213> ORGANISM: Artificial Sequence
<220> FEATURE:
<223> OTHER INFORMATION: GPNMB4

<400> SEQUENCE: 58

Met Asp Ser Gln Ala Gln Val Leu Met Leu Leu Leu Leu Trp Val Ser
1               5                   10                  15

Gly Thr Cys Gly Gln Ser Val Leu Thr Gln Pro Pro Ser Ala Ser Gly
            20                  25                  30

Thr Pro Gly Gln Arg Val Thr Ile Ser Cys Ser Gly Ser Ser Ser Asn
        35                  40                  45

Ile Gly Asn Asn Tyr Val Ser Trp Tyr Gln Gln Leu Pro Gly Thr Ala
    50                  55                  60

Pro Lys Leu Leu Ile Tyr Ala Asp Ser Gln Arg Pro Ser Gly Val Pro
65                  70                  75                  80

Asp Arg Phe Ser Gly Ser Lys Ser Gly Thr Ser Ala Ser Leu Ala Ile
                85                  90                  95

Ser Gly Leu Arg Ser Glu Asp Glu Ala Asp Tyr Tyr Cys Gly Ala Trp
            100                 105                 110

Asp Ser Ser Leu Asn Ala Tyr Val Phe Gly Gly Gly Thr Lys Leu Thr
        115                 120                 125

Val Leu Gly Gln Pro Lys Ala Asn Pro Thr Val Thr Leu Phe Pro Pro
    130                 135                 140

Ser Ser Glu Glu Leu Gln Ala Asn Lys Ala Thr Leu Val Cys Leu Ile
145                 150                 155                 160

Ser Asp Phe Tyr Pro Gly Ala Val Thr Val Ala Trp Lys Ala Asp Gly
                165                 170                 175

Ser Pro Val Lys Ala Gly Val Glu Thr Thr Lys Pro Ser Lys Gln Ser
            180                 185                 190

Asn Asn Lys Tyr Ala Ala Ser Ser Tyr Leu Ser Leu Thr Pro Glu Gln
        195                 200                 205

Trp Lys Ser His Arg Ser Tyr Ser Cys Gln Val Thr His Glu Gly Ser
    210                 215                 220

Thr Val Glu Lys Thr Val Ala Pro Thr Glu Cys Ser Gly Gly Gly Ser
225                 230                 235                 240

Gly Gly Gly Ser Glu Gly Gly Ser Glu Gly Gly Ser Glu Gly
                245                 250                 255

Gly Gly Ser Glu Gly Gly Ser Gly Gly Ser Gly Glu Val Gln
            260                 265                 270

Leu Leu Glu Ser Gly Gly Gly Leu Val Gln Pro Gly Gly Ser Leu Arg
        275                 280                 285

Leu Ser Cys Ala Ala Ser Gly Phe Thr Phe Gln Arg Tyr Pro Met Ser
    290                 295                 300

Trp Val Arg Gln Ala Pro Gly Lys Gly Leu Glu Trp Val Ser Ser Ile
305                 310                 315                 320

Ser His Ser Gly Gly Ser Lys Tyr Tyr Ala Asp Ser Val Lys Gly Arg
                325                 330                 335

Phe Thr Ile Ser Arg Asp Asn Ser Lys Asn Thr Leu Tyr Leu Gln Met
            340                 345                 350

Asn Ser Leu Arg Ala Glu Asp Thr Ala Val Tyr Tyr Cys Ala Arg Lys
```

-continued

```
                355                 360                 365
Trp Ser Thr Phe Asp Tyr Trp Gln Gly Thr Leu Val Thr Val Ser
    370                 375                 380

Ser
385

<210> SEQ ID NO 59
<211> LENGTH: 385
<212> TYPE: PRT
<213> ORGANISM: Artificial Sequence
<220> FEATURE:
<223> OTHER INFORMATION: GPNMB5

<400> SEQUENCE: 59

Met Asp Ser Gln Ala Gln Val Leu Met Leu Leu Leu Trp Val Ser
1               5                   10                  15

Gly Thr Cys Gly Gln Ser Val Leu Thr Gln Pro Pro Ser Ala Ser Gly
            20                  25                  30

Thr Pro Gly Gln Arg Val Thr Ile Ser Cys Ser Gly Ser Ser Ser Asn
            35                  40                  45

Ile Gly Asn Asn Tyr Val Ser Trp Tyr Gln Gln Leu Pro Gly Thr Ala
50                  55                  60

Pro Lys Leu Leu Ile Tyr Ala Asp Ser Gln Arg Pro Ser Gly Val Pro
65                  70                  75                  80

Asp Arg Phe Ser Gly Ser Lys Ser Gly Thr Ser Ala Ser Leu Ala Ile
                85                  90                  95

Ser Gly Leu Arg Ser Glu Asp Glu Ala Asp Tyr Tyr Cys Gly Ala Trp
            100                 105                 110

Asp Ser Ser Leu Asn Ala Tyr Val Phe Gly Gly Gly Thr Lys Leu Thr
            115                 120                 125

Val Leu Gly Gln Pro Lys Ala Asn Pro Thr Val Thr Leu Phe Pro Pro
    130                 135                 140

Ser Ser Glu Glu Leu Gln Ala Asn Lys Ala Thr Leu Val Cys Leu Ile
145                 150                 155                 160

Ser Asp Phe Tyr Pro Gly Ala Val Thr Val Ala Trp Lys Ala Asp Gly
                165                 170                 175

Ser Pro Val Lys Ala Gly Val Glu Thr Thr Lys Pro Ser Lys Gln Ser
            180                 185                 190

Asn Asn Lys Tyr Ala Ala Ser Ser Tyr Leu Ser Leu Thr Pro Glu Gln
        195                 200                 205

Trp Lys Ser His Arg Ser Tyr Ser Cys Gln Val Thr His Glu Gly Ser
    210                 215                 220

Thr Val Glu Lys Thr Val Ala Pro Thr Glu Cys Ser Gly Gly Gly Ser
225                 230                 235                 240

Gly Gly Gly Ser Glu Gly Gly Ser Glu Gly Gly Ser Glu Gly
                245                 250                 255

Gly Gly Ser Glu Gly Gly Ser Gly Gly Ser Gly Glu Val Gln
            260                 265                 270

Leu Leu Glu Ser Gly Gly Gly Leu Val Gln Pro Gly Gly Ser Leu Arg
        275                 280                 285

Leu Ser Cys Ala Ala Ser Gly Phe Thr Phe Ile Arg Arg Pro Met Ser
    290                 295                 300

Trp Val Arg Gln Ala Pro Gly Lys Gly Leu Glu Trp Val Ser Ser Ile
305                 310                 315                 320

Ser His Ser Gly Gly Ser Lys Tyr Tyr Ala Asp Ser Val Lys Gly Arg
```

```
                    325                 330                 335
Phe Thr Ile Ser Arg Asp Asn Ser Lys Asn Thr Leu Tyr Leu Gln Met
                340                 345                 350

Asn Ser Leu Arg Ala Glu Asp Thr Ala Val Tyr Tyr Cys Ala Arg Lys
            355                 360                 365

Trp Ser Thr Phe Asp Tyr Trp Gly Gln Gly Thr Leu Val Thr Val Ser
        370                 375                 380

Ser
385

<210> SEQ ID NO 60
<211> LENGTH: 385
<212> TYPE: PRT
<213> ORGANISM: Artificial Sequence
<220> FEATURE:
<223> OTHER INFORMATION: GPNMB6

<400> SEQUENCE: 60

Met Asp Ser Gln Ala Gln Val Leu Met Leu Leu Leu Trp Val Ser
1               5                   10                  15

Gly Thr Cys Gly Gln Ser Val Leu Thr Gln Pro Pro Ser Ala Ser Gly
            20                  25                  30

Thr Pro Gly Gln Arg Val Thr Ile Ser Cys Ser Gly Ser Ser Ser Asn
        35                  40                  45

Ile Gly Asn Asn Tyr Val Ser Trp Tyr Gln Gln Leu Pro Gly Thr Ala
    50                  55                  60

Pro Lys Leu Leu Ile Tyr Ala Asp Ser Gln Arg Pro Ser Gly Val Pro
65                  70                  75                  80

Asp Arg Phe Ser Gly Ser Lys Ser Gly Thr Ser Ala Ser Leu Ala Ile
                85                  90                  95

Ser Gly Leu Arg Ser Glu Asp Glu Ala Asp Tyr Tyr Cys Gly Ala Trp
            100                 105                 110

Asp Ser Ser Leu Asn Ala Tyr Val Phe Gly Gly Gly Thr Lys Leu Thr
        115                 120                 125

Val Leu Gly Gln Pro Lys Ala Asn Pro Thr Val Thr Leu Phe Pro Pro
    130                 135                 140

Ser Ser Glu Glu Leu Gln Ala Asn Lys Ala Thr Leu Val Cys Leu Ile
145                 150                 155                 160

Ser Asp Phe Tyr Pro Gly Ala Val Thr Val Ala Trp Lys Ala Asp Gly
                165                 170                 175

Ser Pro Val Lys Ala Gly Val Glu Thr Thr Lys Pro Ser Lys Gln Ser
            180                 185                 190

Asn Asn Lys Tyr Ala Ala Ser Ser Tyr Leu Ser Leu Thr Pro Glu Gln
        195                 200                 205

Trp Lys Ser His Arg Ser Tyr Ser Cys Gln Val Thr His Glu Gly Ser
    210                 215                 220

Thr Val Glu Lys Thr Val Ala Pro Thr Glu Cys Ser Gly Gly Gly Ser
225                 230                 235                 240

Gly Gly Gly Ser Glu Gly Gly Ser Glu Gly Gly Ser Glu Gly
                245                 250                 255

Gly Gly Ser Glu Gly Gly Ser Gly Gly Ser Gly Glu Val Gln
            260                 265                 270

Leu Leu Glu Ser Gly Gly Gly Leu Val Gln Pro Gly Gly Ser Leu Arg
        275                 280                 285

Leu Ser Cys Ala Ala Ser Gly Phe Thr Phe Ala Ala Arg Pro Met Ser
```

```
                    290                 295                 300
Trp Val Arg Gln Ala Pro Gly Lys Gly Leu Glu Trp Val Ser Ser Ile
305                 310                 315                 320

Ser His Ser Gly Gly Ser Lys Tyr Tyr Ala Asp Ser Val Lys Gly Arg
                325                 330                 335

Phe Thr Ile Ser Arg Asp Asn Ser Lys Asn Thr Leu Tyr Leu Gln Met
                340                 345                 350

Asn Ser Leu Arg Ala Glu Asp Thr Ala Val Tyr Tyr Cys Ala Arg Lys
                355                 360                 365

Trp Ser Thr Phe Asp Tyr Trp Gly Gln Gly Thr Leu Val Thr Val Ser
                370                 375                 380

Ser
385

<210> SEQ ID NO 61
<211> LENGTH: 385
<212> TYPE: PRT
<213> ORGANISM: Artificial Sequence
<220> FEATURE:
<223> OTHER INFORMATION: GPNMB7

<400> SEQUENCE: 61

Met Asp Ser Gln Ala Gln Val Leu Met Leu Leu Leu Trp Val Ser
1               5                   10                  15

Gly Thr Cys Gly Gln Ser Val Leu Thr Gln Pro Pro Ser Ala Ser Gly
                20                  25                  30

Thr Pro Gly Gln Arg Val Thr Ile Ser Cys Ser Gly Ser Ser Ser Asn
                35                  40                  45

Ile Gly Asn Asn Tyr Val Ser Trp Tyr Gln Gln Leu Pro Gly Thr Ala
50                  55                  60

Pro Lys Leu Leu Ile Tyr Asp Thr Pro Leu Arg Pro Ser Gly Val Pro
65                  70                  75                  80

Asp Arg Phe Ser Gly Ser Lys Ser Gly Thr Ser Ala Ser Leu Ala Ile
                85                  90                  95

Ser Gly Leu Arg Ser Glu Asp Glu Ala Asp Tyr Tyr Cys Gly Ala Trp
                100                 105                 110

Asp Ser Ser Leu Asn Ala Tyr Val Phe Gly Gly Asp Thr Lys Leu Thr
                115                 120                 125

Val Leu Gly Gln Pro Lys Ala Asn Pro Thr Val Thr Leu Phe Pro Pro
                130                 135                 140

Ser Ser Glu Glu Leu Gln Ala Asn Lys Ala Thr Leu Val Cys Leu Ile
145                 150                 155                 160

Ser Asp Phe Tyr Pro Gly Ala Val Thr Val Ala Trp Lys Ala Asp Gly
                165                 170                 175

Ser Pro Val Lys Ala Gly Val Glu Thr Thr Lys Pro Ser Lys Gln Ser
                180                 185                 190

Asn Asn Lys Tyr Ala Ala Ser Ser Tyr Leu Ser Leu Thr Pro Glu Gln
                195                 200                 205

Trp Lys Ser His Arg Ser Tyr Ser Cys Gln Val Thr His Glu Gly Ser
                210                 215                 220

Thr Val Glu Lys Thr Val Ala Pro Thr Glu Cys Ser Gly Gly Gly Ser
225                 230                 235                 240

Gly Gly Gly Ser Glu Gly Gly Ser Glu Gly Gly Ser Gly Ser Glu Gly
                245                 250                 255

Gly Gly Ser Glu Gly Gly Gly Ser Gly Gly Gly Ser Gly Glu Val Gln
```

-continued

```
                260                 265                 270
Leu Leu Glu Ser Gly Gly Leu Val Gln Pro Gly Gly Ser Leu Arg
            275                 280             285

Leu Ser Cys Ala Ala Ser Gly Phe Thr Phe Ser Asn Tyr Ala Met Ser
        290             295                 300

Trp Val Arg Gln Ala Pro Gly Lys Gly Leu Glu Trp Val Ser Ser Ile
305                 310             315                     320

Ser His Ser Gly Gly Ser Lys Tyr Tyr Ala Asp Ser Val Lys Gly Arg
                325             330                 335

Phe Thr Ile Ser Arg Asp Asn Ser Lys Asn Thr Leu Tyr Leu Gln Met
            340                 345             350

Asn Ser Leu Arg Ala Glu Asp Thr Ala Val Tyr Tyr Cys Ala Arg Lys
        355             360                 365

Trp Ser Thr Phe Asp Tyr Trp Gly Gln Gly Thr Leu Val Thr Val Ser
    370                 375             380

Ser
385
```